United States Patent
Hibri et al.

(10) Patent No.: US 10,028,839 B2
(45) Date of Patent: Jul. 24, 2018

(54) PERCUTANEOUS IMPLANTABLE NUCLEAR PROSTHESIS

(71) Applicant: SPINAL STABILIZATION TECHNOLOGIES, LLC, San Antonio, TX (US)

(72) Inventors: Nadi Salah Hibri, San Antonio, TX (US); James Douglas Lutz, San Antonio, TX (US)

(73) Assignee: Spinal Stabilization Technologies, LLC, San Antonio, TX (US)

( * ) Notice: Subject to any disclaimer, the term of this patent is extended or adjusted under 35 U.S.C. 154(b) by 0 days.

(21) Appl. No.: 15/457,194

(22) Filed: Mar. 13, 2017

(65) Prior Publication Data

US 2017/0246005 A1    Aug. 31, 2017

Related U.S. Application Data

(63) Continuation of application No. 14/098,352, filed on Dec. 5, 2013, now Pat. No. 9,592,130, which is a
(Continued)

(51) Int. Cl.
  *A61F 2/44*    (2006.01)
  *A61F 2/46*    (2006.01)
  *A61F 2/30*    (2006.01)

(52) U.S. Cl.
  CPC ............ *A61F 2/441* (2013.01); *A61F 2/442* (2013.01); *A61F 2/4611* (2013.01);
(Continued)

(58) Field of Classification Search
  CPC ................................. A61F 2/441; A61F 2/442
  See application file for complete search history.

(56) References Cited

U.S. PATENT DOCUMENTS

| | | | |
|---|---|---|---|
| 3,875,595 A | 4/1975 | Froning | 623/17.12 |
| 5,192,326 A | 3/1993 | Bao et al. | 623/17.12 |

(Continued)

FOREIGN PATENT DOCUMENTS

| | | |
|---|---|---|
| KR | 20120040309 | 4/2012 |
| WO | WO 2007/087404 | 8/2007 |

OTHER PUBLICATIONS

Birkenmaier et al., "Minimally Invasive Endoscopic Spinal Surgery," www.snineuniverse.com/disolavarticle.nho/ariicle 2016.html [Jun. 15, 2009].
(Continued)

*Primary Examiner* — Nicholas Woodall
(74) *Attorney, Agent, or Firm* — Norton Rose Fulbright US LLP

(57) ABSTRACT

An inter-vertebral disc prosthesis intended for percutaneous deployment comprises an expandable annular enclosure and an expandable nuclear enclosure. The expandable annular enclosure incorporates a reinforcing annular band along its periphery and is filled with in-situ curable rubber. The expandable nuclear enclosure is filled with a gas. The nuclear prosthesis further incorporates a novel, integrally molded sealing valve assembly and is stretchable and collapsible into a minimal profile for ease of insertion into a specially designed delivery cannula, and is inflation-assisted expandable into an inter-vertebral disc in which complete percutaneous nuclectomy has been performed.

18 Claims, 17 Drawing Sheets

Related U.S. Application Data continuation of application No. 12/753,524, filed on Apr. 2, 2010, now Pat. No. 8,636,803.

(60) Provisional application No. 61/212,104, filed on Apr. 7, 2009.

(52) U.S. Cl.
CPC .............. *A61F 2002/30069* (2013.01); *A61F 2002/30563* (2013.01); *A61F 2002/30583* (2013.01); *A61F 2002/30584* (2013.01); *A61F 2002/30586* (2013.01); *A61F 2002/444* (2013.01)

(56) References Cited

U.S. PATENT DOCUMENTS

| | | | |
|---|---|---|---|
| 5,439,464 A | 8/1995 | Shapiro | 606/83 |
| 5,571,189 A | 11/1996 | Kuslich | 623/17.12 |
| 5,645,597 A | 7/1997 | Krapiva | 606/279 |
| 5,674,295 A | 10/1997 | Ray et al. | 623/17.12 |
| 5,702,449 A | 12/1997 | McKay | 623/17.16 |
| 5,865,845 A | 2/1999 | Thalgott | 623/17.16 |
| 5,888,220 A | 3/1999 | Felt et al. | 128/898 |
| 5,890,268 A | 4/1999 | Mullen et al. | 29/527.5 |
| 5,981,826 A | 11/1999 | Ku et al. | 623/23.72 |
| 5,990,378 A | 11/1999 | Ellis | 623/11.11 |
| 6,127,597 A | 10/2000 | Beyer et al. | 606/86 R |
| 6,264,695 B1 | 7/2001 | Stay | 623/17.16 |
| 6,332,894 B1 | 12/2001 | Stalcup et al. | 623/17.11 |
| 6,375,682 B1 | 4/2002 | Fleishmann et al. | 623/17.12 |
| 6,390,992 B1 | 5/2002 | Morris et al. | 600/585 |
| 6,395,032 B1 | 5/2002 | Gauchet | 623/17.12 |
| 6,419,704 B1 | 7/2002 | Ferree | 623/17.12 |
| 6,436,143 B1 | 8/2002 | Ross et al. | 623/17.16 |
| 6,482,234 B1 | 11/2002 | Weber et al. | 623/17.12 |
| 6,527,804 B1 | 3/2003 | Gauchet et al. | 623/17.12 |
| 6,596,008 B1 | 7/2003 | Kambin | 606/190 |
| 6,712,853 B2 | 3/2004 | Kuslich | 623/17.16 |
| 6,733,532 B1 | 5/2004 | Gauchet et al. | 623/17.12 |
| 6,852,095 B1 | 2/2005 | Ray | 604/93.01 |
| 6,866,681 B2 | 5/2005 | Laboureau et al. | 623/13.2 |
| 6,893,466 B2 | 5/2005 | Trieu | 623/17.16 |
| 6,958,077 B2 | 10/2005 | Suddaby | 623/17.11 |
| 6,969,404 B2 | 11/2005 | Ferree | 623/17.11 |
| 7,001,431 B2 | 2/2006 | Bao et al. | 623/17.12 |
| 7,004,971 B2 | 2/2006 | Serhan et al. | 623/17.16 |
| 7,008,427 B2 | 3/2006 | Sevrain | 606/71 |
| 7,056,345 B2 | 6/2006 | Kuslich | 623/17.16 |
| 7,077,865 B2 | 7/2006 | Bao et al. | 623/17.12 |
| 7,133,001 B2 | 11/2006 | Mrstik et al. | 343/915 |
| 7,182,783 B2 | 2/2007 | Trieu | 623/17.12 |
| 7,201,751 B2 | 4/2007 | Zucherman et al. | 606/249 |
| 7,201,776 B2 | 4/2007 | Ferree et al. | 623/17.12 |
| 7,204,851 B2 | 4/2007 | Trieu et al. | 623/17.11 |
| 7,220,282 B2 | 5/2007 | Kuslich | 623/17.16 |
| 7,273,497 B2 | 9/2007 | Ferree | 623/17.12 |
| 7,309,359 B2 | 12/2007 | Trieu et al. | 623/17.16 |
| 7,632,294 B2 | 12/2009 | Milbodker et al. | 606/297 |
| 7,722,612 B2 | 5/2010 | Sala et al. | 606/79 |
| 7,842,055 B2 | 11/2010 | Pintor et al. | 606/159 |
| 7,972,351 B2 | 7/2011 | Trinidad | 606/194 |
| 7,993,351 B2 | 8/2011 | Worley et al. | 606/129 |
| 8,066,758 B2 | 11/2011 | Bogert et al. | 623/1.13 |
| 8,133,250 B2 | 3/2012 | Parsonage et al. | 606/194 |
| 8,142,489 B2 | 3/2012 | Doran et al. | 623/1.15 |
| 2002/0026244 A1 | 2/2002 | Trieu | 623/17.16 |
| 2002/0147497 A1 | 10/2002 | Belef et al. | 623/17.12 |
| 2003/0028251 A1 | 2/2003 | Mathews | 623/17.16 |
| 2003/0199979 A1 | 10/2003 | McGuckin, Jr. | 623/17.11 |
| 2004/0106999 A1 | 6/2004 | Mathews | 623/17.16 |
| 2004/0186471 A1 | 9/2004 | Trieu | 606/914 |
| 2004/0230309 A1 | 11/2004 | DiMauro et al. | 623/17.12 |
| 2005/0015150 A1 | 1/2005 | Lee | 623/17.12 |
| 2005/0055099 A1 | 3/2005 | Ku | 623/17.16 |
| 2005/0065609 A1 | 3/2005 | Wardlaw | 623/17.12 |
| 2005/0090901 A1 | 4/2005 | Studer | 623/17.12 |
| 2005/0197702 A1 | 9/2005 | Coppes et al. | 623/17.12 |
| 2005/0249771 A1 | 11/2005 | Malaviya et al. | 424/423 |
| 2005/0251259 A1 | 11/2005 | Suddaby | 623/17.12 |
| 2005/0278029 A1 | 12/2005 | Trieu | 623/17.16 |
| 2006/0247780 A1 | 11/2006 | Bert | 623/17.16 |
| 2006/0293749 A1 | 12/2006 | Hudgins et al. | 623/17.11 |
| 2007/0060924 A1 | 3/2007 | Choi | 606/93 |
| 2007/0073402 A1 | 3/2007 | Vresilovic et al. | 623/17.12 |
| 2007/0093906 A1 | 4/2007 | Hudgins et al. | 623/17.16 |
| 2007/0135921 A1 | 6/2007 | Park | 623/17.12 |
| 2007/0150061 A1 | 6/2007 | Trieu | 623/17.12 |
| 2007/0162136 A1 | 7/2007 | O'Neil et al. | 623/17.12 |
| 2007/0168031 A1 | 7/2007 | Hudgins et al. | 623/17.12 |
| 2007/0173935 A1 | 7/2007 | O'Neil et al. | 623/17.11 |
| 2007/0173940 A1 | 7/2007 | Hestad et al. | 623/17.12 |
| 2007/0213732 A1 | 9/2007 | Khanna et al. | 606/86 A |
| 2007/0255406 A1 | 11/2007 | Trieu | 623/17.11 |
| 2007/0270953 A1 | 11/2007 | Trieu | 623/17.11 |
| 2008/0046082 A1 | 2/2008 | Lee | 623/17.16 |
| 2008/0058932 A1 | 3/2008 | Trieu et al. | 623/17.11 |
| 2008/0154367 A1 | 6/2008 | Justis et al. | 623/11.11 |
| 2008/0154368 A1 | 6/2008 | Justis et al. | 623/11.11 |
| 2008/0154373 A1 | 6/2008 | Protopsaltis et al. | 623/17.12 |
| 2008/0288074 A1 | 11/2008 | O'Neil et al. | 623/17.16 |
| 2009/0012618 A1 | 1/2009 | Ahrens et al. | 623/17.12 |
| 2009/0112323 A1 | 4/2009 | Hestad et al. | 623/17.12 |
| 2010/0030216 A1 | 2/2010 | Arcenio | 606/79 |
| 2010/0256619 A1 | 10/2010 | Teitelbaum et al. | 606/15 |
| 2010/0256766 A1 | 10/2010 | Hibri et al. | 623/17.16 |
| 2011/0190753 A1 | 8/2011 | Forrest | 606/27 |
| 2011/0196499 A1 | 8/2011 | Boucher et al. | 623/17.16 |
| 2011/0264224 A1 | 10/2011 | Ferree | 623/17.16 |
| 2012/0089229 A1 | 4/2012 | Thramann | 623/17.16 |
| 2012/0277862 A1 | 11/2012 | Tornier et al. | 623/17.13 |

OTHER PUBLICATIONS

International Search Report dated Jun. 17, 2014 for International Application No. PCT/US2014/019911, filed Mar. 3, 2014.

International Search Report dated Jun. 19, 2014 for International Application No. PCT/US2014/019887, filed Mar. 3, 2014.

International Search Report dated Jun. 25, 2014 for International Application No. PCT/US2014/019957, filed Mar. 3, 2014.

Sharma et al., "Manufacturing of Doubly Curved Tubular Composite Structures: Mapping and Weave Modifications", *Thermoplastic Composite Materials*, 15:209-225 (May 2002).

Viscocliosi et al., "Beyond Total Disc: The Future of Spine Surgery", *Spine Non-Fusion, Musculoskeletal Investment Research*, pp. 1-289 (May 2004).

Wu et al., "The direct effect of graft compliance mismatch per se on development of host arterial intimal hyperplasia at the anastomotic interface", *Annals of Vascular Surgery*, 7(2):156-168 (Mar. 1993).

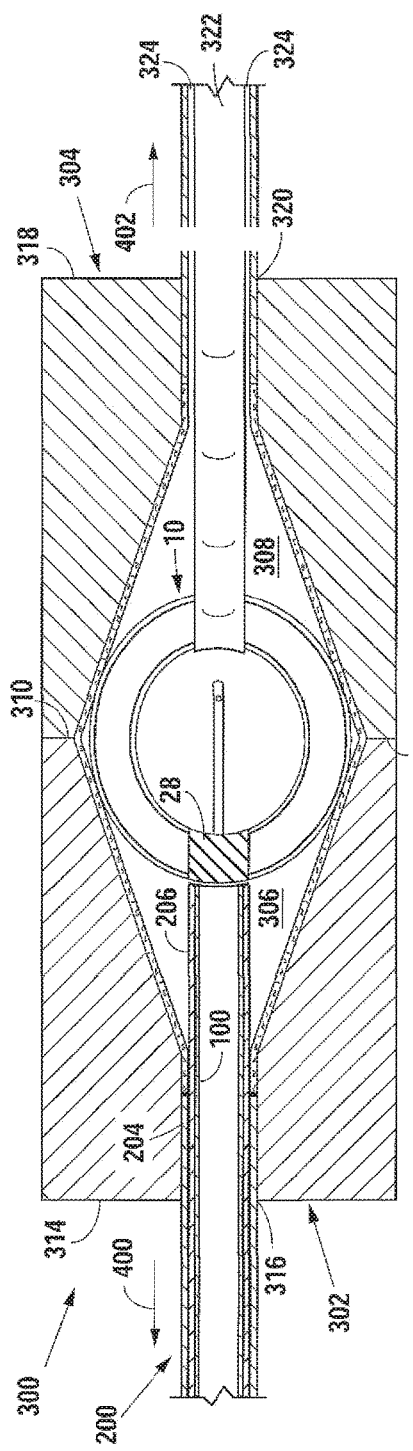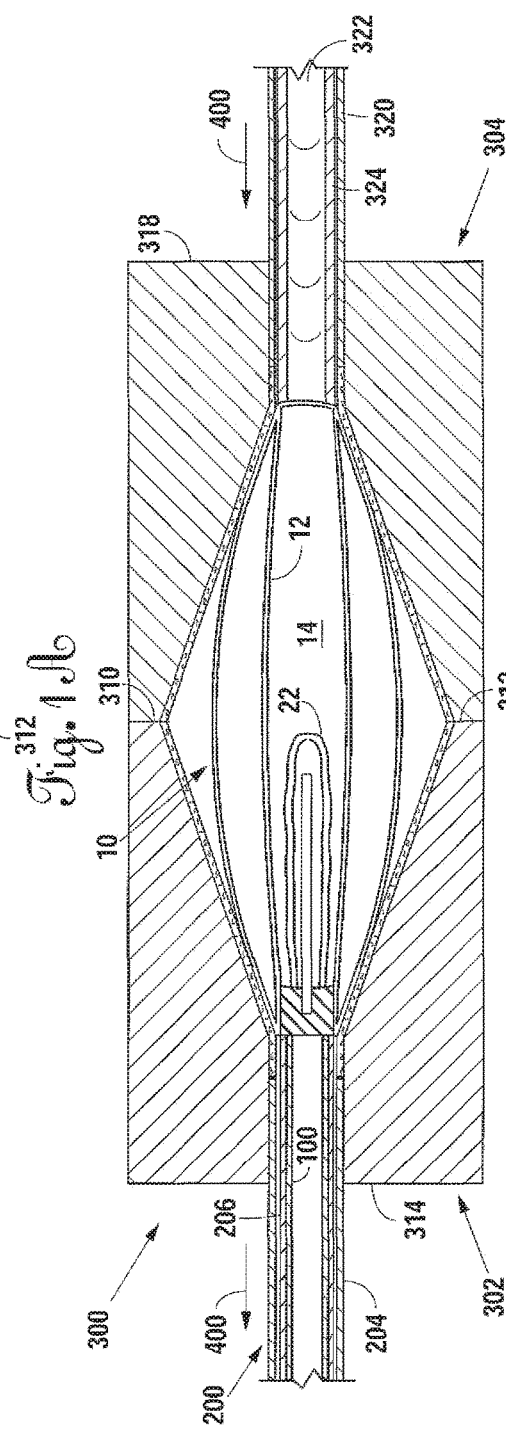

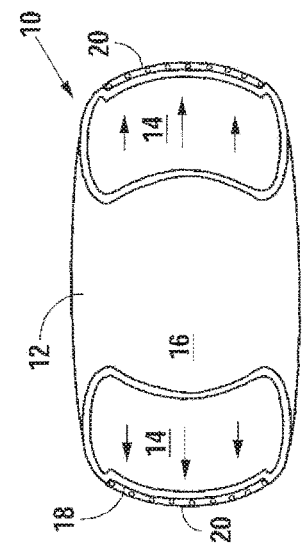
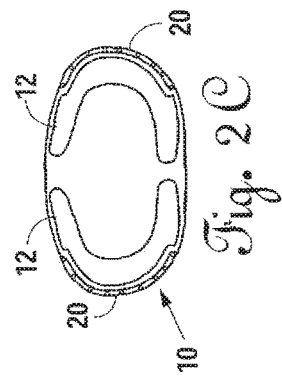
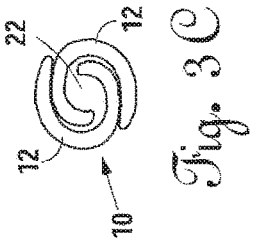
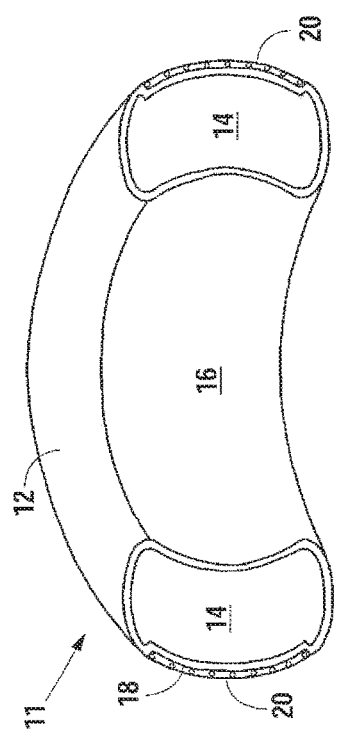
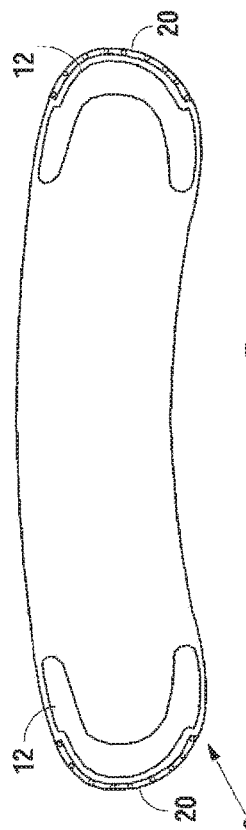

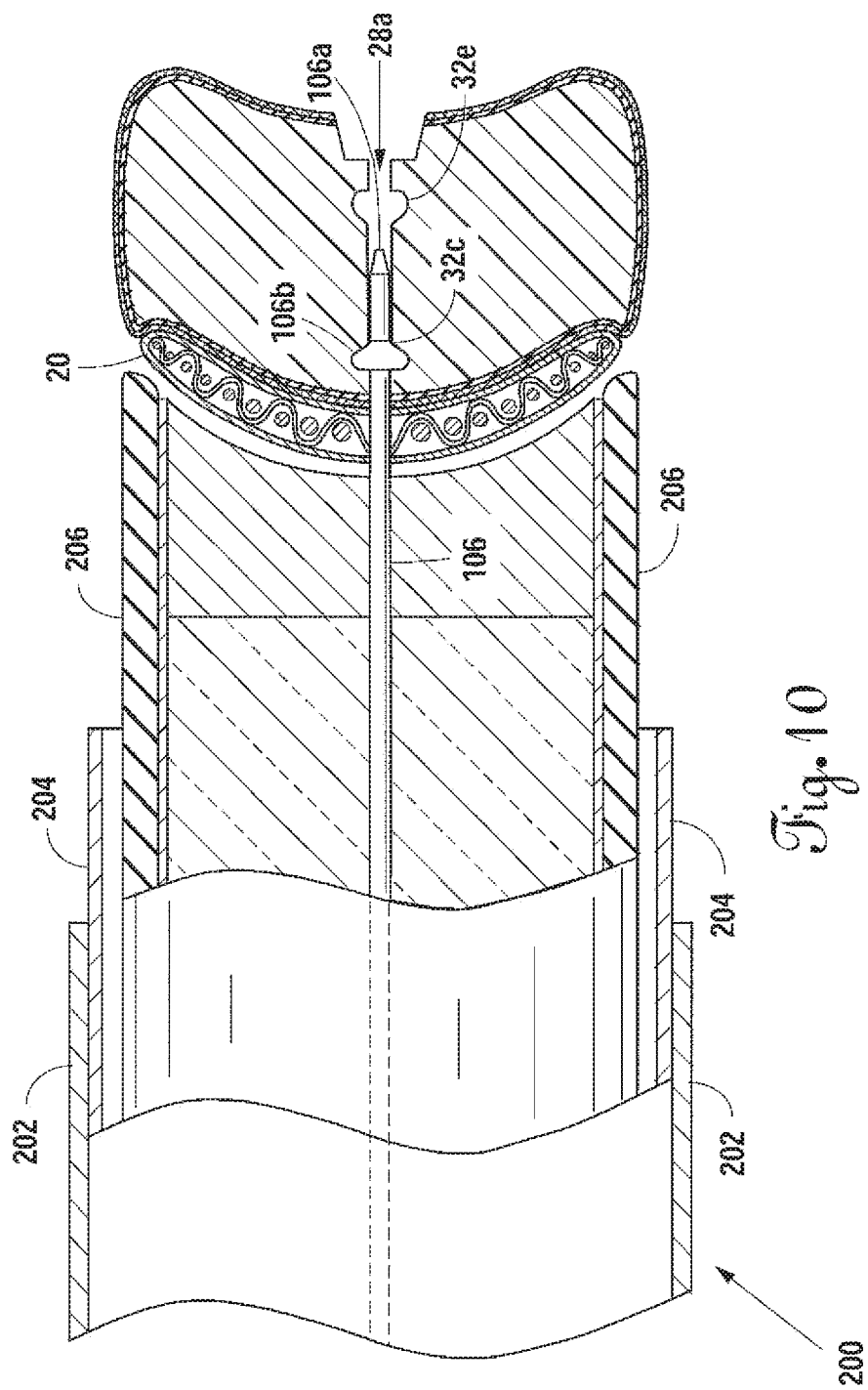

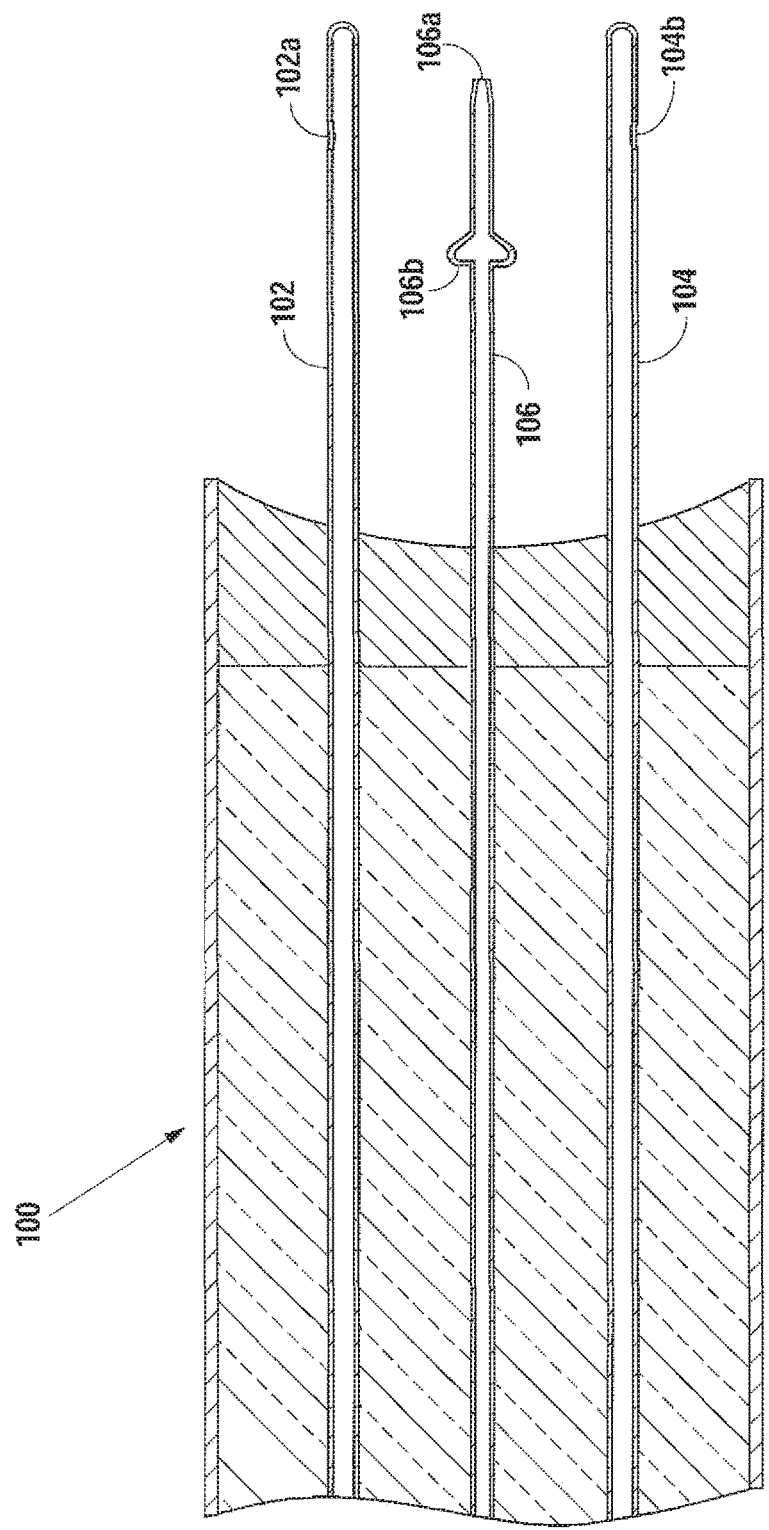

PERCUTANEOUS IMPLANTABLE NUCLEAR PROSTHESIS

CROSS REFERENCE TO RELATED APPLICATIONS

This application is a continuation of U.S. patent application Ser. No. 14/098,352, filed Dec. 5, 2013, which is a continuation of U.S. patent application Ser. No. 12/753,524, filed Apr. 2, 2010, which claims the benefit of U.S. Provisional Application No. 61/212,104 filed Apr. 7, 2009, the contents of which applications are incorporated herein by reference.

BACKGROUND OF THE INVENTION

1. Field of the Invention

The present invention generally relates to body-implantable devices. More particularly, the present invention relates to a percutaneously insertable and expandable inter-vertebral disc prosthesis. Specifically, the present invention comprises a novel nuclear prosthesis, a specially designed delivery apparatus, and a loading apparatus for loading the nuclear prosthesis within the delivery apparatus.

2. Description of the Related Art

The role of the inter-vertebral disc in spine biomechanics has been the subject of extensive research and is generally well understood. A typical native spinal unit is shown for exemplary purposes in FIG. 22A. The functional spinal unit, or spinal motion segment 500 consists of two adjacent vertebrae 502 and 504, the inter-vertebral disc 506 and the adjacent ligaments (not shown). The components of the disc are the nucleus pulposus 506a, the annulus fibrosis 506b, and the vertebral end-plates 506c. These components act in synchrony and their integrity is crucial for optimal disc function. During axial loading of the normal native disc 506, the pressure of the nucleus pulposus 506a rises, transmitting vertical force on the end plates 506c and outward radial stress on the annulus fibrosis 506b, as shown by the direction arrows in FIG. 22A. The vertical stress is transformed to tensile forces in the fibers of the annulus fibrosis 506b. Because the gelatinous nucleus pulposus 506a is deformable but noncompressible, it flattens radially, and the annulus fibrosis 506b bulges and stretches uniformly. Flexion of the spine involves the compression of the anterior annulus fibrosis 506b, as well as the nucleus pulposus 506a. The nucleus pulposus 506a deforms and migrates, posteriorly stretching the annular fibers and expanding radially. Thus, the nucleus pulposus 506a and annulus fibrosis 506b function synergistically as a cushion by reorienting vertical forces radially in a centrifugal direction.

The native vertebral end plate 506c prevents the nucleus pulposus from bulging into the adjacent vertebral body by absorbing considerable hydrostatic pressure that develops from mechanical loading of the spine. The end plate 506c is a thin layer of hyaline fibrocartilage with subchondral bone plate, typically around 1 millimeter thick. The outer 30% of the end plate 506c consists of dense cortical bone and is the strongest area of the end plate 506c. The end plate 506c is thinnest and weakest in the central region adjacent to the nucleus pulposus.

With aging and repetitive trauma, the components of the inter-vertebral disc 506 undergo biochemical and biomechanical changes and can no longer function effectively, resulting in a weakened inter-vertebral disc 506. As the disc 506 desiccates and becomes less deformable, the physical and functional distinction between the nucleus pulposus 506a and the annulus fibrosis 506b becomes less apparent. Disc desiccation is associated with loss of disc space height and pressure. The annulus fibrosis 506b loses its elasticity. The apparent strength of the vertebral end-plates 506e decreases and vertebral bone density and strength are diminished. This leads the end-plates 506c to bow into the vertebral body, imparting a biconcave configuration to the vertebral body. Uneven stresses are created on the end plates 506c, annulus fibrosis 506b, ligaments (not shown), and facet joints (not shown), leading to back pain. At this point, the annulus fibrosis 506b assumes an inordinate burden of tensile loading and stress, and this further accelerates the process of degeneration of the annulus fibrosis 506b. Fissuring of the annulus fibrosis 506b further diminishes its elastic recoil, preventing the annulus fibrosis 506b from functioning as a shock absorber. Leakage of the nuclear material can cause irritation of the nerve roots by both mechanical and biochemical means. Eventually, degenerative instability is created, leading to both spinal canal and neuroforaminal stenosis.

Historically, spine surgery consisted of simple decompressive procedures. The advent of spinal fusion and the proliferation of surgical instrumentation and implants has led to an exponential utilization of expensive new technologies. As an alternative to open surgical discectomy and fusion, Minimally Invasive Spinal Surgery (MISS) has been advocated. Thus far, the primary rationale for favoring the MISS approach has been to lessen postoperative pain, limit the collateral damage to the surrounding tissues, and hasten the recovery process rather than affect long term outcomes. Despite the lack of clear superiority and outcome data, these technologies have continued to flourish.

However, many spinal surgeons remain skeptical about the positive claims regarding MISS, citing certain drawbacks, including increase in operating room time, requirement for expensive proprietary instruments, increased cost, and the technically demanding nature of the procedure. Despite the advantage of a minimal incision approach, MISS requires an adequate decompression and/or fusion procedure in order to have results comparable to traditional open surgical approaches.

Ideally, a nuclectomy and implant insertion would be performed through a percutaneous posterolateral approach. Advantages of the percutaneous posterolateral approach over conventional open surgery and MISS include obviating the need for surgically exposing, excising, removing, or injuring interposed tissues; preservation of epidural fat; avoiding epidural scarring, blood loss, and nerve root trauma. Other advantages include minimizing "access surgery" and hospitalization costs, and accelerating recovery. A percutaneous procedure may be expeditiously used on an outpatient basis in selected patients. On the other hand, percutaneous insertion imposes a number of stringent requirements on the nuclear prosthesis and its method of delivery.

Several devices have been used to fill the inter-vertebral space void following discectomy in order to prevent disc space collapse. These devices generally fall into two categories: fusion prostheses and motion prostheses. Fusion prostheses intended for MISS insertion offer few if any advantages over those for open surgical technique. While these types of implants eliminate pathological motion, they also prevent normal biomechanical motion at the treated segment. Greater degrees of stress are transmitted above and below the treated segment, often leading to accelerated degeneration of adjacent discs, facet joints, and ligaments (adjacent level degeneration).

Motion prostheses generally aim at restoring disc height, shock absorption, and range of motion, thus alleviating pain. Artificial motion prostheses may be divided into two general types: the total disc prosthesis and the nucleus prosthesis. The total disc prosthesis is designed for surgical insertion, replacing the entire disc, while the nucleus prosthesis is designed for replacing only the nucleus pulposus, and generally may be inserted by open surgical or MISS methods.

Prior designs of motion nucleus prostheses include enclosures that are filled with a diverse variety of materials to restore and preserve disc space height while permitting natural motion. However, there are several shortcomings of prior nucleus motion prostheses designs. Some of the prior nucleus motion prostheses require surgical approaches for insertion that involve removal of a significant amount of structural spinal elements including the annulus fibrosis. Removal of these structural spinal elements causes destabilization of the spinal segment. Prior nuclear motion prosthesis designs also fail to provide the outer margin of the nuclear prosthesis with surface and structural properties that encourage native tissue ingrowth. Instead, such prostheses are made from generally non-porous materials that impede full incorporation of the nuclear prosthesis into the surrounding annular margin.

Some prior designs have annular bands along the outer periphery of the nucleus motion prostheses. However, prior annular bands are non-compliant. This is disadvantageous because it reduces the radial outer expansion required for load dampening. Thus, the load is transferred to the end plates of the vertebrae, which can withstand only limited deformation. The result is that the end plates eventually fail, resulting in loss of intradiscal pressure, accelerated degeneration, and subsidence of the nuclear prosthesis. Other prostheses do not have an annular band. These prostheses tend to exert untoward pressure on an already weakened annulus fibrosis. Particularly, such a prosthesis tends to protrude into a pre-existing annular tear.

Other designs fail to incorporate or use a central gas cushion with a valve system or assembly that does not leak. Still others concentrate the harder load bearing component of the nuclear prosthesis in the central aspect of the disc, predisposing the nuclear prosthesis to subsidence. Another problem with prior nuclear motion prostheses is the imprecise sizing and tailoring of the nuclear prosthesis. Over sizing places unnecessary stress on the already damages and degenerated annulus fibrosis, while under sizing of the nuclear prosthesis may result in inadequate contact with the inner wall of the annulus fibrosis, and possibly non-integration and migration of the nuclear prosthesis. Other designs of nucleus motion prostheses suffer draw backs such as bulkiness, inelasticity, inability to fold and pack the nuclear prosthesis into a delivery cannula or apparatus for percutaneous implantation into a patient. In fact, percutaneous delivery of a motion nucleus prosthesis heretofore, has been unavailable.

Applicants here propose to overcome the disadvantages of the prior designs of nucleus motion prostheses by providing a multi-compartment nuclear prosthesis having a semi-compliant annular reinforcement band disposed adjacent or contiguously around the periphery of a rubber filled annular enclosure. The annular enclosure nests a central, gas cushioned nuclear enclosure and an integrated sealing valve assembly. The nuclear prosthesis of the present invention is foldable to fit within a delivery apparatus, and is intended for percutaneous insertion into a nuclear space void following percutaneous total nuclectomy. Once percutaneously inserted, the nuclear prosthesis is expandable by an inflation-assisting device to provide cushioning and stability to a spinal segment weakened by degeneration.

SUMMARY OF THE INVENTION

The present invention overcomes the deficiencies of prior nuclear motion prostheses, offers several advantageous properties, and provides a system for sizing, forming, delivering, and deploying a nuclear prosthesis into the inter-vertebral disc space. The percutaneously implantable nuclear prosthesis, formed in accordance with the present invention, utilizes the advantages of both a textile prosthesis and a polymer prosthesis to create a compartmentalized composite structure, having characteristics closely resembling the properties of a healthy native inter-vertebral disc. The nuclear prosthesis is comprised of an annular structure and a nuclear structure. The annular structure comprises an annular enclosing layer which defines an annular enclosure, an annular reinforcement band adjacent the periphery of the annular enclosing layer, a sealing valve core disposed within the annular enclosure and adjacently attached to the annular enclosing layer, and in-situ curable rubber, which is injected into the annular enclosure. The nuclear structure comprises a nuclear enclosing layer which defines a nuclear enclosure and an indwelling catheter mounted and bonded to a neck portion of the nuclear enclosing layer, and extends distally into, and is enclosed within the nuclear enclosure.

Referring to FIG. 22B the structure of the nuclear prosthesis comprising the annular structure 11 filled with the deformable, but not compressible in-situ curable rubber and the nuclear structure 21 centrally located within the annular structure 11 and being filled with a compressible gas allows for the vertical and horizontal load stresses placed on the inter-vertebral disc space to be redirected inward, centrally toward the nuclear structure 21 (see direction arrows of FIG. 22B), instead of outward. Moreover, annular structure 11 has a biocompatible outer annular reinforcement band that encourages tissue in-growth of the native annulus fibrosis 506b, thereby providing reinforcement to the native annulus fibrosis.

According to the present invention, there is provided a percutaneously insertable and detachable nuclear prosthesis having an annular enclosing layer that defines an annular enclosure. The annular enclosing layer is made of an annular tubular elastomeric membrane, is contiguous along its outer periphery with a textile annular reinforcement band, and incorporates a sealing valve core. Central to the annular enclosing layer is a nuclear enclosing layer defining a nuclear enclosure. The nuclear enclosing layer has a neck region. The neck region of the nuclear enclosing layer defines an open mouth that receives an indwelling catheter. The neck region is mounted on the indwelling catheter. The indwelling catheter is a tube that defines a lumen. The indwelling catheter is coupled to a sealing valve core which is disposed within the annular enclosure, and has its lumen plugged by a sealing plug after inflation within the inter-vertebral disc space.

The nuclear prosthesis is detachably mounted to a distal end of an inflation stylus and is loaded within a distal end of a delivery apparatus. The inflation stylus has three inflation tubes projecting from the distal end of the inflation stylus and slidably insertable through the sealing valve core of the sealing valve assembly. The sealing valve core is formed of a resilient material and has three pathways being defined by three parallel channels extended through the sealing valve core. Upon insertion of the three inflation tubes of the inflation stylus through the channels of the sealing valve core, the pathways take the form of cylindrical apertures in precise mating alignment with the inflation tubes of the inflation stylus to provide fluid-tight seal against and around the outer surfaces of the inflation tubes. The central inflation tube is a nuclear access tube that provides pressurized fluid to the nuclear enclosure. One of the outer tubes is an annular inlet tube that provides pressurized fluid to the annular enclosure through an inlet port provided in the sealing valve core. The other outer tube is an annular outlet tube that receives pressurized fluid from the annular enclosure through an outlet port provided in the sealing valve core.

The annular inlet tube and the annular outlet tube have side pores in the walls of the tubes adjacent the closed tips of the tubes whereby in-situ vulcanizing rubber flows through the side pore in the annular inlet tube into one end of the annular enclosure and back through the side pore of the annular outlet tube, and into the inflation stylus. After inflation of the annular enclosure and nuclear enclosure, the inflation stylus can be efficiently disengaged from the sealing valve core, and upon withdrawal thereof, the pathways return to an elongated slit or channel configuration to provide a fluid tight seal for the inflated nuclear prosthesis.

It is, therefore, a general object of the present invention to provide a nuclear prosthesis which exhibits an optimal overall combination of physical, viscoelastic, and other properties superior to previous designs of motion nucleus prostheses.

It is another object of the present invention to provide a nuclear prosthesis that is fundamentally reliable and durable, and utilizes the latest in surface modification technology to enhance the bio-compatibility, bio-durability, infection resistance, and other aspects of performance.

It is another object of the present invention to provide a nuclear prosthesis that reduces stress on the vulnerable central portions of the native vertebral end plates.

It is another object of the present invention to reduce the stress on the vulnerable central portions of the native vertebral end plates by providing a nuclear prosthesis that redirects the vector of forces caused by load stress inward, toward the core or center of the nuclear prosthesis. In this regard, the present invention provides a gas-filled central enclosure to aide in load bearing, cushioning, shock absorption and stabilization by directing the vector of forces toward the gas-filled central enclosure. The present invention redirects both lateral and vertical forces toward the gas-filled central enclosure, thereby providing protection to the vertebral end plates. The present invention accomplishes the redirection of vector forces by having a non-compliant annular reinforcement band along the outer periphery of the nuclear prosthesis, and a compressible gas filled central nuclear enclosure.

It is yet another object of the present invention to provide a nuclear prosthesis that provides reinforcement and structural support to the native annulus fibrosis. The annular reinforcement band of the present invention encourages native tissue in-growth of the native annulus fibrosis to provide added stabilization and reinforcement.

It is still another object of the present invention to provide a nuclear prosthesis wherein the compliance of the nuclear prosthesis increases progressively toward the center of the nuclear prosthesis. Each component of the nuclear prosthesis is tailored to provide suitable viscoelastic properties that contribute to the overall performance of the nuclear prosthesis. This arrangement is intended to relieve the stress on the native annulus fibrosis by redirecting the radial outer vector of forces centrally toward the nuclear enclosure. The nuclear prosthesis is thus rendered iso-elastic with respect to the spinal segment.

Yet another object of the present invention is to provide a nuclear prosthesis that has expansion tailorability. The nuclear prosthesis can be expanded to variable sizes to accommodate the dimensions of the evacuated nuclear space. The nuclear enclosing layer, annular enclosing layer and annular reinforcement band possess the ability to be first inflated or stretched to its unextended or working profile and then, there-beyond to a limited extent and/or controlled extent by the application of greater pressure. The controlled flexibility of the textile annular reinforcement band and the expansion of the annular and nuclear enclosures can accommodate a wider range of nuclear space dimensions, reducing the need to precisely match the nuclear prosthesis to the nuclear space as to size.

It is yet a further object of the present invention to provide an inflation-assisted expandable nuclear prosthesis that distracts the disc space, and supports and reinforces the annulus fibrosis while keeping the ligaments and facet joints in a taut condition.

It is another object of the present invention to provide a novel sealing valve assembly which has a sealing valve core integrally bonded to the annular enclosing layer within the annular enclosure, having a mounting region adapted on its inner margin for fluid tight bonding to an indwelling catheter lying within the nuclear enclosure. The sealing valve core of the sealing valve assembly is detachably connected to the tip of the delivery apparatus and is self-sealing upon removal of the inflation stylus.

It is another object of the present invention to provide a nuclear prosthesis which can be geometrically and elastically deformed to reduce its axial and transverse diameter through radial elongation, into a minimal profile for ease of insertion into the delivery apparatus, while minimizing the risks that could be associated with such flexibility. This is achieved by the components of the nuclear prosthesis being suitably configured and dimensioned to fond a perfect mating fit to each other and to the nuclear enclosing layer. The annular reinforcement layer, annular enclosing layer and nuclear enclosing layer must cooperate in a synchronized fashion to achieve a precise folded and wrapped configuration. The folding of the nuclear prosthesis is further achieved by minimizing the combined thicknesses of the annular enclosing layer and nuclear enclosing layer and optimizing the longitudinal flexibility and radial compliance of the annular reinforcement band by careful selection of the type of bio-compatible yarn, the number of layers, the heat set conditions, and the angles at which braids are formed. The folding of the nuclear prosthesis is also aided by the selection and use of a semi-compliant medical balloon material for the annular and nuclear enclosing layers.

It is further an object of the present invention to provide a nuclear prosthesis that has a porous outer margin thereby facilitating the incorporation of the nuclear prosthesis into the nuclear space.

It is yet another object of the present invention to provide a delivery apparatus having an assembly of coaxial telescoping cannulas with the nuclear prosthesis disposed therein, and a method of delivering the nuclear prosthesis percutaneously to the nuclear space. The delivery apparatus houses and carries the folded nuclear prosthesis within its delivery cannula. The delivery cannula also houses and incorporates an inflation stylus defining three tubes in fluid communication with the three chambers or pathways of the sealing valve core of the nuclear prosthesis. Within the delivery cannula is a specially designed release cannula adjacent the sealing valve core to release the inflation stylus from the nuclear prosthesis.

A typical procedure for implantation of the nuclear prosthesis involves performing an initial percutaneous nuclectomy through a percutaneous access device, insertion of the delivery apparatus within the percutaneous access device, insertion of the delivery cannula carrying the nuclear prosthesis and deploying the nuclear prosthesis within the nuclear space void. In deployment, the annular and nuclear enclosures are expanded using any suitable fluid delivery system, allowing the nuclear prosthesis to assume a substantially discoid shape as the nuclear prosthesis radially and axially expands and substantially conforms to the shape of the nuclear space void.

The annular and nuclear enclosures are inflated simultaneously with a pressurized liquid until adequate disc space distraction is achieved and a predetermined pressure level within the nuclear prosthesis is achieved. The annular enclosure is inflated with an in-situ curable rubber, and the nuclear enclosure is inflated with a liquid such as saline. After curing of the in-situ curable rubber within the annular enclosure occurs, the liquid within the nuclear enclosure is replaced with a compressible gas. Nitrogen, carbon dioxide, or many other suitable gases can be used within the nuclear enclosure. At this point, the indwelling catheter is plugged with a sealing plug introduced into the indwelling catheter and pushed therein. The delivery cannula is detached from the sealing valve core by the release cannula, and the delivery apparatus is then removed.

These and other objects, aspects, features and advantages of the present invention will be clearly understood and explained with reference to the accompanying drawings and through consideration of the following detailed description.

DESCRIPTION OF THE DRAWINGS

FIG. 1A is a sectional side view of the loading apparatus of the present invention with an inflated nuclear prosthesis of the present invention therein;

FIG. 1B is a sectional side view of an inflated annular enclosing layer of the nuclear prosthesis of the present invention;

FIG. 1C is a sectional side view of an inflated annular enclosing layer of the nuclear prosthesis of the present invention;

FIG. 2A is a sectional side view of the loading apparatus of the present invention with a partially deflated nuclear prosthesis of the present invention therein;

FIG. 2B is a sectional side view of the annular enclosing layer of the nuclear prosthesis of the present invention in a partially stretched position during loading into the delivery apparatus;

FIG. 2C is a sectional side view of the nuclear prosthesis of the present invention in a partially deflated state;

FIG. 3A is a sectional side view of the loading apparatus of the present invention showing the loading of a deflated nuclear prosthesis of the present invention onto the delivery apparatus of the present invention;

FIG. 3C is a sectional side view of the nuclear prosthesis showing the folding of the annular enclosing layer around the nuclear enclosing layer when the nuclear prosthesis is deflated;

FIG. 10 is a sectional side view of the inflation stylus of the present invention and the of the nuclear prosthesis of the present invention showing interaction of the nuclear access tube with the indwelling catheter;

FIG. 11 is a sectional top view of the inflation stylus of the present invention;

FIG. 11A is a sectional top view of the inflation stylus of the present invention and the of the nuclear prosthesis of the present invention showing interaction of the tubes of the inflation stylus with the ports and pathways of the sealing valve core;

DESCRIPTION OF THE INVENTION

Figure 20:
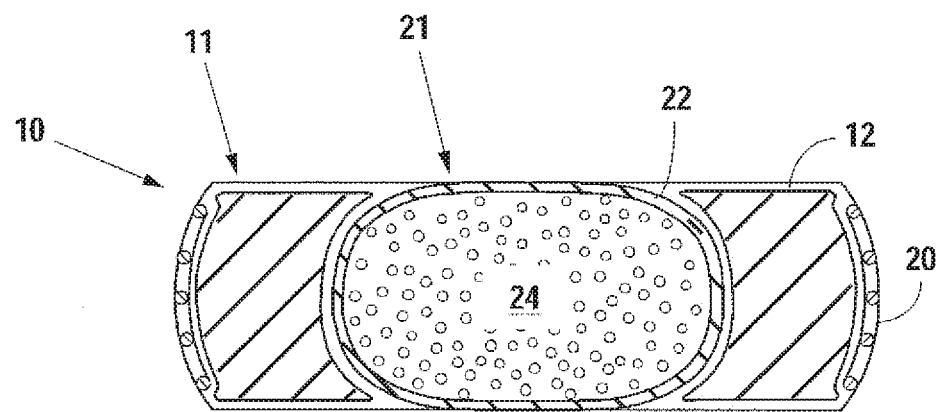
FIG. 20 is a sectional side view of the nuclear prosthesis of the present invention after delivery and inflation with fluid within the patient.
Figure 21:
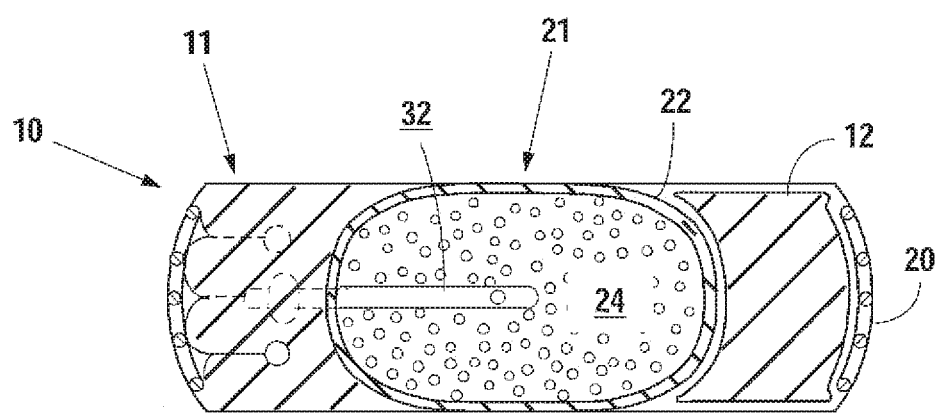
FIG. 21 is a sectional side view of the nuclear prosthesis of the present invention after delivery and inflation with fluid within the patient.
Figure 22A:
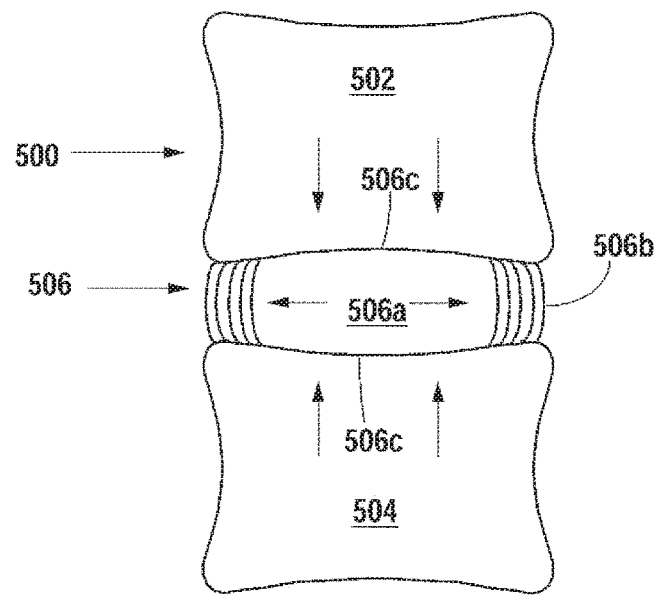
FIG. 22A is a rear view of a native inter-vertebral disc space showing the direction of dispersion of typical horizontal and vertical load forces.
Figure 22B:
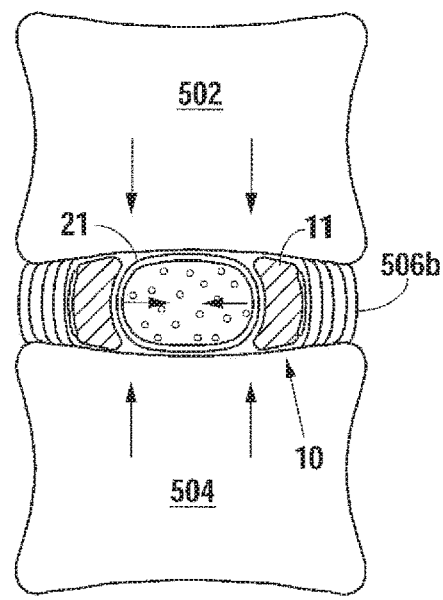
FIG. 22B is a rear view of an inter-vertebral disc space with the nuclear prosthesis of the present invention therein, showing redirection of dispersion of typical horizontal and vertical load forces by the nuclear prosthesis of the present invention.

Referring to FIGS. 1 through 4 the nuclear prosthesis 10 of the present invention is disclosed. Nuclear prosthesis 10 comprises an annular structure 11 and a nuclear structure 21. Annular structure 11 comprises an annular enclosing layer 12 defining an annular enclosure 14, and nuclear structure 21 comprises a nuclear enclosing layer 22 defining a nuclear enclosure 24. Nuclear enclosing layer 22 is disposed adjacent annular enclosing layer 12 in the central space defined by annular enclosing layer 12, along an inner margin 16 thereof. Annular structure 11 of nuclear prosthesis 10 further comprises an annular reinforcement band 20 contiguous with or adjacent a peripheral or outer margin 18 of the inflatable annular enclosing layer 12 and a sealing valve core 28 of a sealing valve assembly 26. Annular enclosing layer 12 incorporates the sealing valve core 28 and annular enclosure 14 filled in-situ with curable rubber. In its inflated state, nuclear prosthesis 10 is substantially discoid in shape, as shown in FIGS. 20 and 21.

Figure 8:
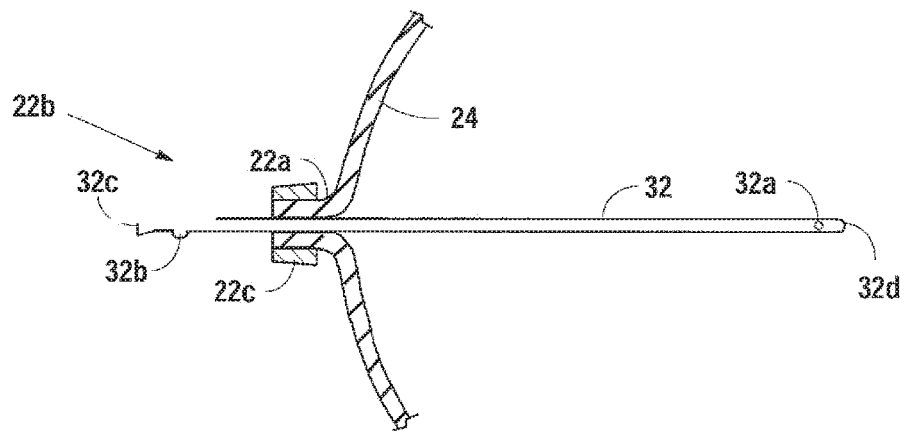
FIG. 8 is a side view of the indwelling catheter and the mounting region of the nuclear enclosing layer of the nuclear prosthesis of the present invention.
Figure 9:
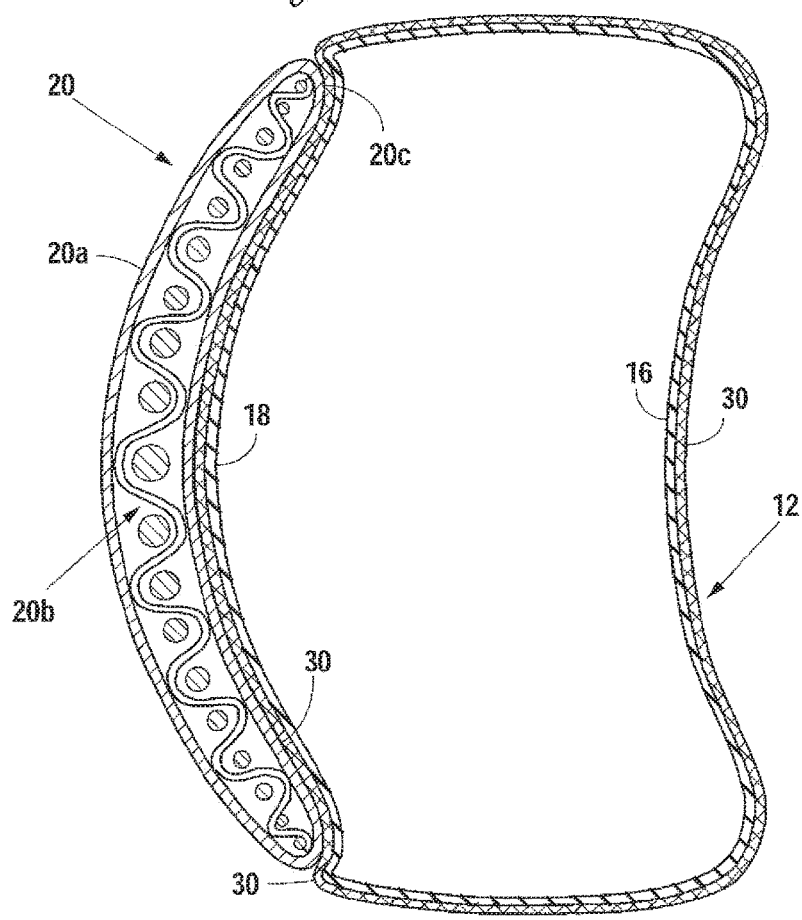
FIG. 9 is a sectional side view of the annular enclosing layer, retaining ring and the layers of the annular reinforcement band of the nuclear prosthesis of the present invention.

Annular enclosure 14 is in communication with an inlet port 36a and an outlet port 38a of sealing valve core 28. Nuclear structure 21 comprises nuclear enclosing layer 22, which defines a discoid inflatable nuclear enclosure 24, and an indwelling catheter 32. A neck portion 22a of nuclear enclosing layer 22 is mounted on indwelling catheter 32, which has a side-pore 32a and a closed tip 32d (see FIG. 8). Nuclear enclosing layer 22 is filled in-situ with compressible gas and converges on a neck portion 22a adapted for fluid-tight bonding to indwelling catheter 32 (see FIG. 8). Returning to FIGS. 1 through 4, indwelling catheter 32 includes a bulbous portion 32b on the proximal end thereof, which is adapted to be coupled within a sealing valve core 28 of sealing valve assembly 26 to a pressurized fluid for inflation of nuclear enclosure 24. Bulbous portion 32b of indwelling catheter 32 is snap-secured and adhesively bonded to sealing valve core 28 so that a fluid-tight connection will be achieved.

Figure 1:
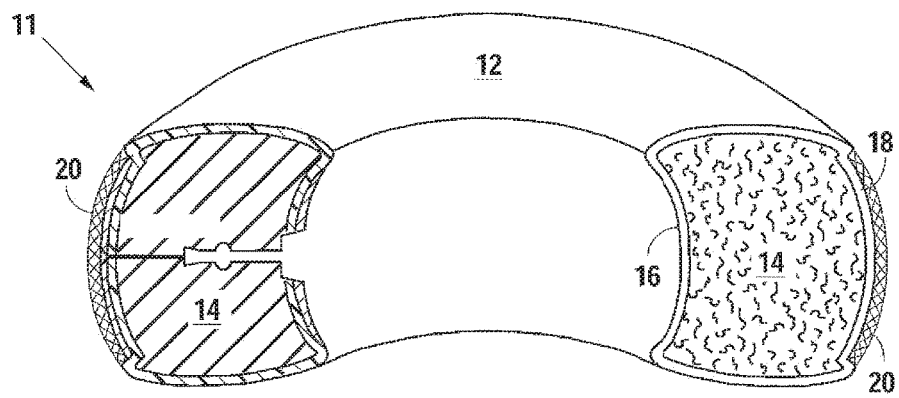
FIG. 1 is a sectional side view of the annular structure of the nuclear prosthesis of the present invention.
Figure 2:
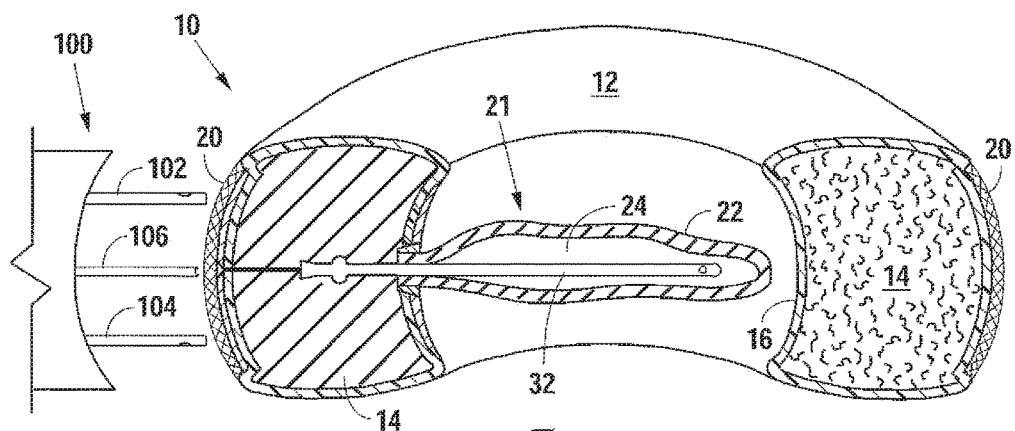
FIG. 2 is a sectional side view of an inflated annular enclosing layer and deflated nuclear enclosing layer of the nuclear prosthesis of the present invention.
Figure 3:
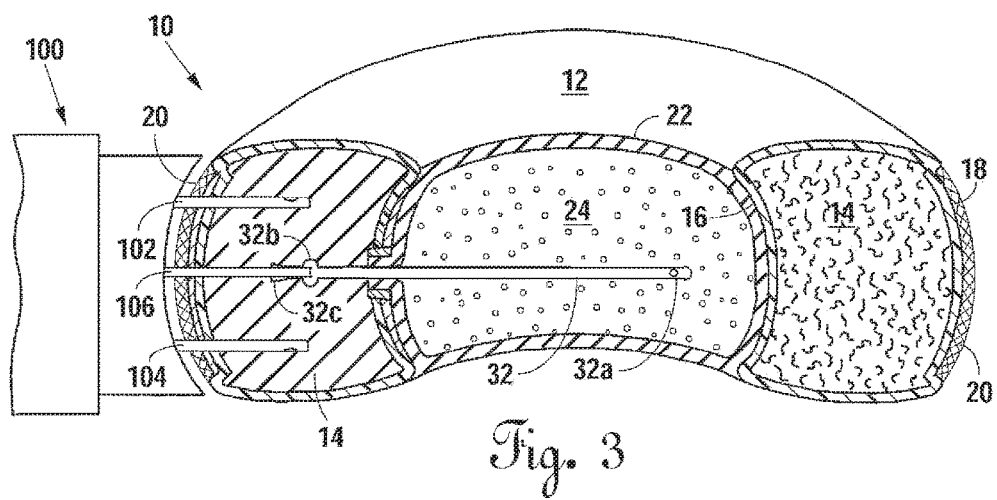
FIG. 3 is a sectional side view of the nuclear prosthesis and the inflation stylus of the present invention.
Figure 3B:
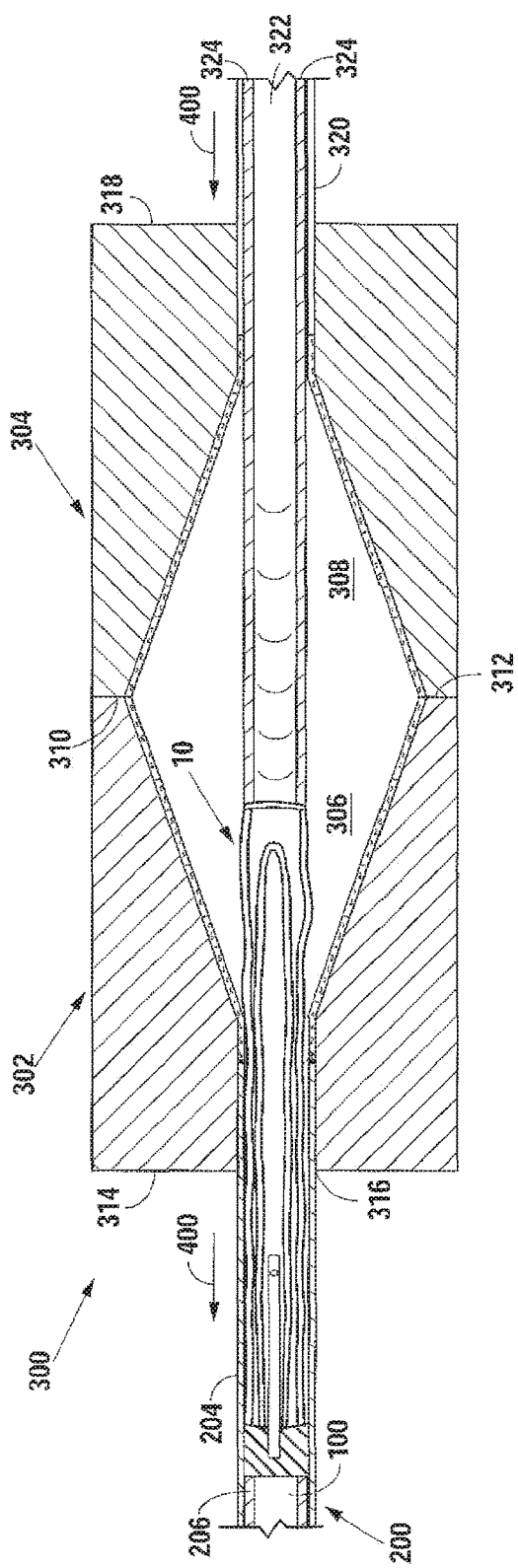
FIG. 3B is a sectional side view of the annular enclosing layer of the nuclear prosthesis of the present invention in a fully stretched position during loading onto the delivery apparatus.
Figure 1D:
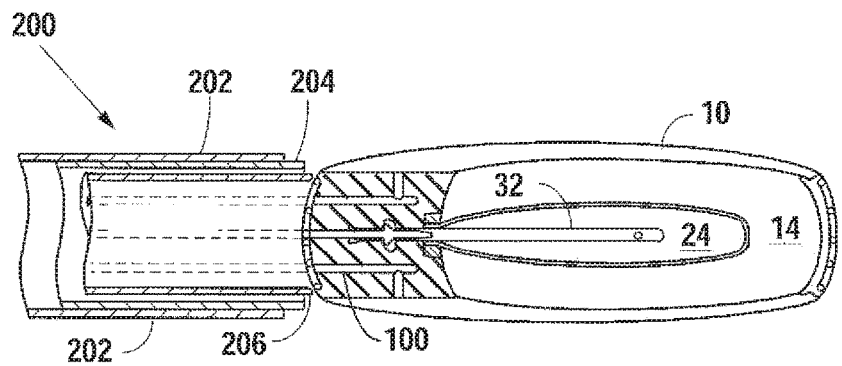
FIG. 1D is a sectional top view of the delivery apparatus of the present invention with the nuclear prosthesis of the present invention loaded therein.
Figure 2D:
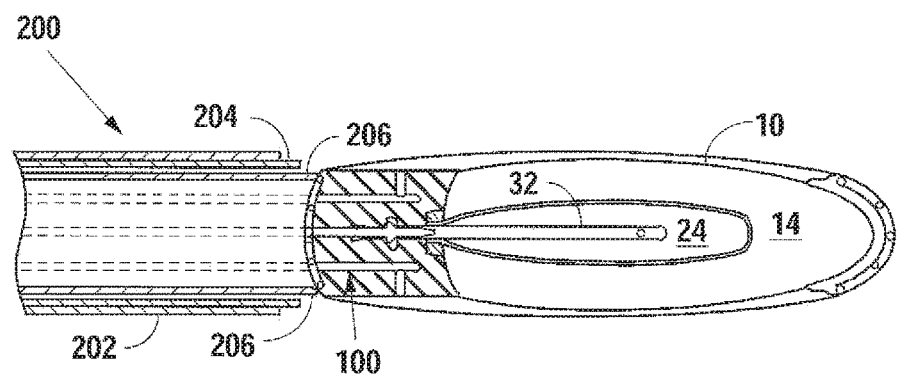
FIG. 2D is a sectional top view of the delivery apparatus of the present invention with the nuclear prosthesis of the present invention loaded thereon.
Figure 3D:
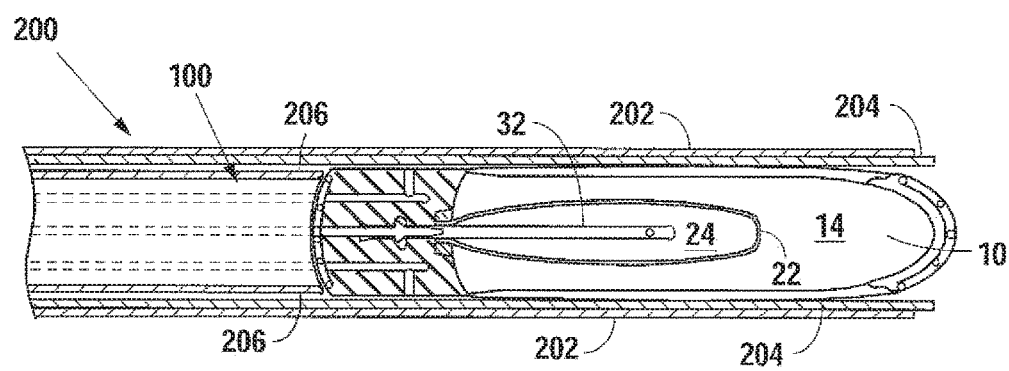
FIG. 3D is a sectional top view of the delivery apparatus of the present invention with the nuclear prosthesis of the present invention loaded thereon and retracted therein, with the delivery apparatus disposed within an access cannula.

Referring to FIGS. 1D, 2D and 3D, a delivery apparatus 200 is disclosed. Delivery apparatus 200 is coaxially and telescopically slidable within an access cannula 202. A distal delivery cannula 204 of delivery apparatus 200 coaxially encloses a release cannula 206 (see FIGS. 10, 11A, 11B and 12) and an inflation stylus 100. Referring to FIGS. 4, 11, 11A and 11B, inflation stylus 100 is a rigid tube with a triple lumen that terminates in three inflation tubes 102, 104 and 106. Inflation tubes 102, 104 and 106 define inflation lumens therein, and are in fluid communication with annular enclosure 14 and nuclear enclosure 24 via sealing valve core 28. The three inflation tubes are an annular inlet tube 102, an annular outlet tube 104 and a nuclear access tube 106. Annular inlet tube 102, annular outlet tube 104 and nuclear access tube 106 project from the distal end of inflation stylus 100 and are detachably secured to three corresponding pathways 36b, 38b and 40, respectively, within sealing valve core 28.

Figure 13:
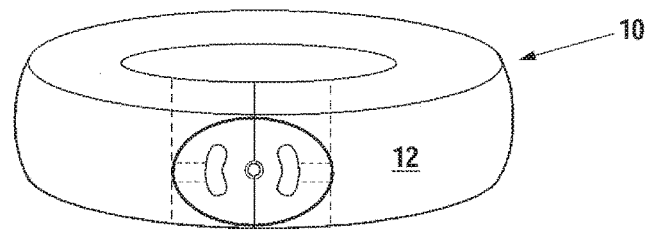
FIG. 13 is a side view along line 12-12 of FIG. 12 showing the connection of the inflation stylus to the of the nuclear prosthesis of the present invention.
Figures 14, 15, 16:
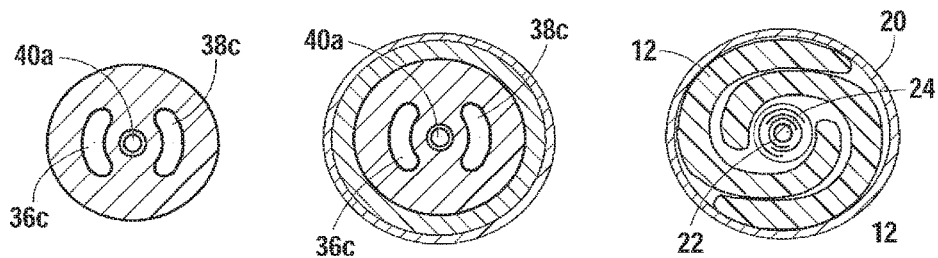
FIG. 14 is a sectional side view showing the connection of the inflation stylus to the of the nuclear prosthesis of the present invention.
FIG. 15 is a sectional side view showing the connection of the inflation stylus to the of the nuclear prosthesis of the present invention.
FIG. 16 is a sectional side view showing the annular enclosing layer folded around the nuclear enclosing layer when the is a sectional side view showing the connection of the inflation stylus to the of the nuclear prosthesis of the present invention is deflated.
Figure 17:
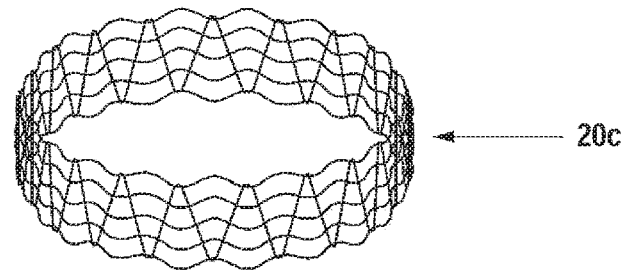
FIG. 17 is a perspective view of the outer layer of the annular reinforcement band of the nuclear prosthesis of the present invention.
Figure 18:
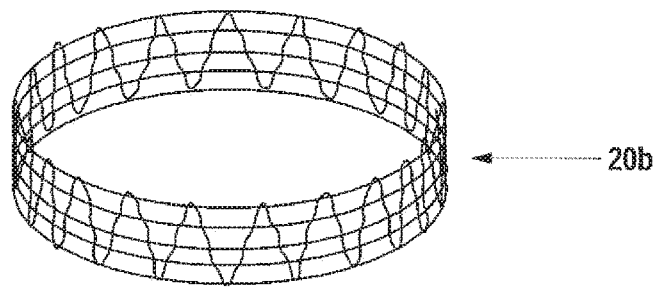
FIG. 18 is a perspective view of one of the middle layers of the annular reinforcement band of the nuclear prosthesis of the present invention.
Figure 19:
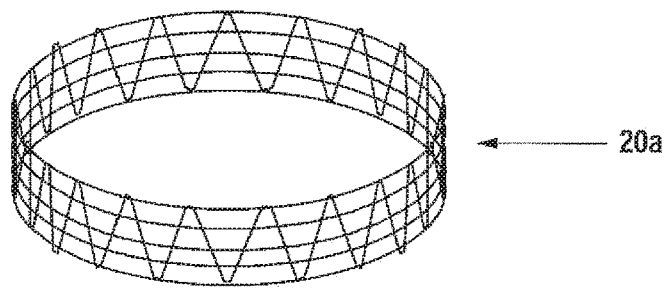
FIG. 19 is a perspective view of the inner layer of the annular reinforcement band of the nuclear prosthesis of the present invention.

Inflation tubes 102, 104 and 106 are adapted to mate with the three corresponding pathways 36b, 38b and 40, respectively, of sealing valve core 28. In order to couple inflation stylus 100 to sealing valve core 28, inflation tubes 102, 104 and 106 are inserted through the inflation bores 36c, 38c and 40a, respectively, which are disposed on the outer margin of sealing valve core 28 (see FIGS. 12 through 14). Inflation tubes 102, 104 and 106 then extend into the slit-like pathways 36b, 38b and 40, respectively.

A fluid-tight communication is formed between annular enclosure 14 through inlet port 36a and outlet port 38a, and through annular inlet tube 102 and annular outlet tube 104. Annular inlet tube 102 has a side pore 102a, and annular outlet tube 104 has a side pore 104a. Side pores 102a and 104a are located towards the closed distal ends of the annular inlet tube 102 and annular outlet tube 104, respectively. Side pore 102a provides a fluid-tight communication with inlet port 36a, and side pore 104a provides a fluid-tight communication with outlet port 38a of sealing valve core 28. A third fluid-tight communication is formed between nuclear enclosure 24 and inflation stylus 100, through nuclear access tube 106, which terminates with an end bore 106a. Nuclear access tube 106 slides through passage 40a and engages a proximal end 32c of indwelling catheter 32.

Referring to FIGS. 4 through 9, 11A and 11B, the design of sealing valve assembly 26 is disclosed. Sealing valve assembly 26 employs sealing valve core 28 which permits the passage of fluid through inlet port 36a, outlet port 38a and indwelling catheter 32, but prevents the flow of fluid through sealing valve core 28 when tubes 102, 104 and 106 are removed from pathways 36b, 38b and 40, respectively. Sealing valve core 28 is formed of a resilient material and contains the three constricted slit-like pathways 36b, 38b and 40 for frictionally engaging the outer surfaces of inflation tubes 102, 104 and 106, respectively, so that a predetermined force is required to withdraw inflation stylus 100 from sealing valve core 28. Pathways 36b, 38b and 40 define passageways through which inflation tubes 102, 104 and 106, respectively, may be inserted without imparting damage to sealing valve core 28.

Sealing valve assembly 26 comprises sealing valve core 28, indwelling catheter 32, and a sealing plug (not shown). Sealing valve core 28 has the general cross-sectional configuration as inflated annular enclosure 14, and is substantially concentric with inflated annular enclosing layer 12. Sealing valve core 28 has an outside diameter which is slightly smaller than the diameter of inflated annular enclosure 14, allowing for additional thickness contributed by annular enclosing layer 12 adjacently enclosing sealing valve core 28. The additional thickness is crucial during loading nuclear prosthesis 10 onto delivery apparatus 200.

Sealing valve core 28 is preferably fabricated by molding from implantable grade elastomeric material (not shown), such that when an in-situ curable rubber such as RTV liquid silicon or other suitable RTV liquid elastomer is injected in-situ into annular enclosure 14, a strong bond is formed between the thermoset silicon of sealing valve core 28 and in the in-situ cured rubber to create a unified load-bearing cushion. Preferably, both sealing valve core 28 and the in-situ curable rubberhave a similar modulus of elasticity.

Figure 11B:
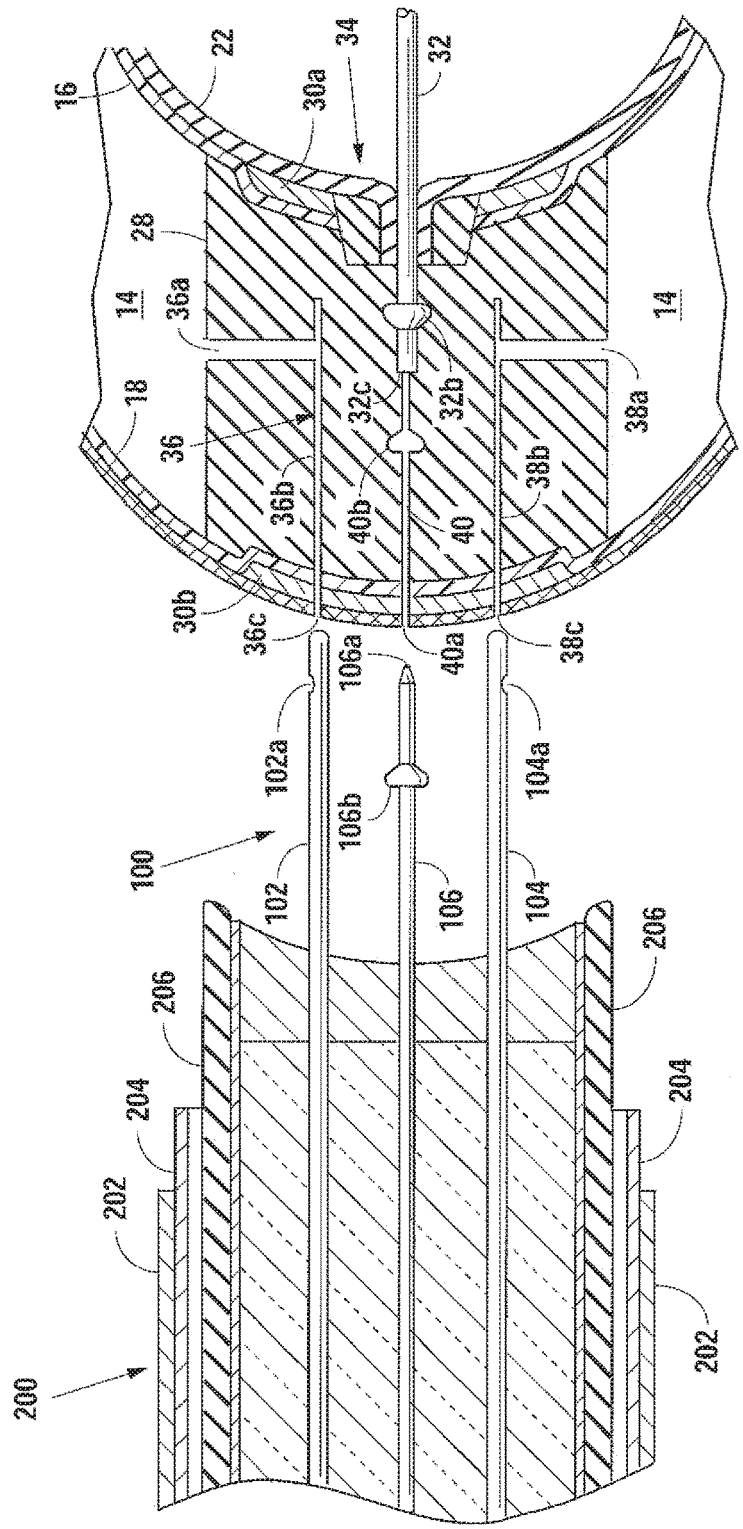
FIG. 11B is a sectional top view of the inflation stylus of the present invention and the of the nuclear prosthesis of the present invention showing interaction of the tubes of the inflation stylus with the ports and pathways of the sealing valve core.

Referring to FIGS. 11A and 11B, sealing valve core 28 detachably mounted on the distal end of inflation stylus 100 is shown. Inflation tubes 102, 104 and 106 at the distal end of inflation stylus 100 are inserted through pathways 36b, 38b and 40, respectively, of sealing valve core 28. In this configuration, side pore 102a of annular inlet tube 102 and side pore 104a of annular outlet tube 104 are in alignment with inlet port 36a and outlet port 38a, respectively, of the sealing valve core 28. Pathways 36b, 38b and 40 in sealing valve core 28 are substantially collapsible such that they take the form of three elongated slits prior to insertion of inflation tubes 102, 104 and 106 therein.

Upon insertion of inflation tubes 102, 104 and 106 through pathways 36b, 38b and 40, respectively, detachable fluid-tight engagement is achieved between inflation tubes 102, 104 and 106 of inflation stylus 100, and annular enclosing layer 12 and nuclear enclosing layer 22. Pathways 36b, 38b and 40 frictionally engage the outer surfaces of inflation tubes 102, 104 and 106, obviating the danger of leakage or dislodgement during the pressuring and inflation of nuclear prosthesis 10, as will discussed in more detail hereinafter.

Referring to FIGS. 5 through 9, 11A and 11B, sealing valve core 28 forms an annular slot 28b, which extends the outer radial circumference of sealing valve core 28. Therefore, annular slot 28b is adjacent both inner margin 16 of annular enclosing layer 12 and outer margin 18 of annular enclosing layer 12. Sealing valve core 28 further forms a nuclear slot 28a within annular slot 28b along the surface of sealing valve core 28 adjacent inner margin 16 of enclosing layer 12. Annular slot 28b and nuclear slot 28a are adapted to receive and retain inner margin 16 of annular enclosing layer 12, respectively, as well as a surrounding retaining ring 30. Thus, along inner margin 16, annular slot 28b and nuclear slot 28a define a nuclear mounting region 28d, which receives annular enclosing layer 12 and retaining ring 30 therein. Annular slot 28b is adapted to receive and retain outer margin 18 of annular enclosing layer, as well as retaining ring 30. Therefore, along outer margin 18, annular slot 28b defines an annular mounting region 28c for receiving and retaining outer margin 18 of enclosing layer and retaining ring 30. The lateral ridges of annular slot 28b along outer margin 18 of annular enclosing layer 12 mate with a flat distal tip of release cannula 206 of delivery apparatus 200 such that when release cannula 206 is held stationary and inflation stylus 100 is retracted, release cannula 206 urges sealing valve core 28 to detach from inflation stylus 100.

Referring to FIGS. 2, 3, 4, and 8, nuclear structure 21 comprises nuclear enclosing layer 12, nuclear enclosure 24 and indwelling catheter 32. Nuclear enclosure 24 is defined by the inflatable nuclear enclosing layer 22, which is bonded about the periphery of indwelling catheter 32. Indwelling catheter 32 is comprised of a catheter body having a bulbous portion 32b disposed on the proximal end 32c of indwelling catheter 32, which is affixed to inner margin 16 of annular enclosing layer 12, and extends within sealing valve core 28. Nuclear enclosing layer 22 is bonded to indwelling catheter 32 at a connector terminal 22b. Connector terminal 22b is defined by neck portion 22a receiving and tightly bonding to the body of indwelling catheter 32 at a predetermined distance from proximal end 32c and bulbous portion 32b of indwelling catheter 32, and a retaining collar 22c receiving and crimping to neck portion 22a and indwelling catheter 32 to provide a fluid-tight seal to nuclear enclosing layer 22.

A fluid-tight seal is formed between indwelling catheter 32 and neck portion 22a of the nuclear enclosing layer 22 by applying a layer of adhesive material (not shown) between indwelling catheter 32 and neck portion 22a of nuclear enclosing layer 22 and crimping retaining collar 22c over indwelling catheter 32 and neck portion 22a to form the sealed connector terminal 22b. Preferably, indwelling catheter 32 and the inner surface of neck portion 22a are thermally and chemically similar, allowing a permanent bond to be performed.

In a preferred embodiment, a polymeric insert (not shown) formed of a mutually bondable material may be interposed between the outer surface of indwelling catheter 32 and inner surface of neck portion 22a of nuclear enclosing layer 22 during the manufacturing process; thus providing for a more durable structural integrity of the attachment. The entire connector terminal 22b including retaining collar 22c, which is placed around neck portion 22a of nuclear enclosing layer 22, is then thermally processed and crimped to sealably bond neck portion 22a of nuclear enclosing layer 22 to indwelling catheter 32. Retaining collar 22c tapers proximally for ease of insertion and bonding into nuclear slot 28a of nuclear mounting region 28b. Indwelling catheter 32 is relatively stiff and may be formed from polyurethane or polyethylene material (not shown) and may include a braided or helically wound wire reinforcing layer (not shown) to resist kinking. In a preferred embodiment, indwelling catheter 32 is formed by extruding a plurality of layers (not shown), including a suitably bondable outer layer (not shown) into a tubular form.

A seal plug (not shown) is inserted into indwelling catheter 32 for obstructing the lumen of indwelling catheter 32 after inflation of nuclear enclosure 24 is complete. The seal plug is prevented from being dislodged from the lumen of indwelling catheter 32 by the constriction of the slit-like pathway 40 of sealing valve core 28 following retraction of inflation stylus 100.

Referring to FIGS. 1 through 3, and FIGS. 1B through 3C, annular enclosing layer 12 has a doughnut-configuration with a substantially concave inner margin 16 and a substantially convex outer margin 18, providing for inward folding of the concave inner margin 16, forming a substantially "C" shaped flat band upon deflation of nuclear prosthesis 10. The substantially "C" shaped flat band configuration of the deflated annular enclosing layer 12 facilitates wrapping annular enclosing layer 12 around the collapsed nuclear enclosing layer 22 and indwelling catheter 32. This configuration also provides for interlocking of nuclear enclosing layer 22 within annular enclosing layer 22 when nuclear prosthesis 10 is inflated.

Annular enclosing layer 12 is preferably made from a polymeric material and defines a fluid-tight annular enclosure 14, which is inflatable with an in-situ curable rubber. Annular enclosing layer 12 is preferably semi-compliant. Desirable attributes of annular enclosing layer 12 are not necessarily identical to desirable attributes for medical balloon catheters (not shown), which are used extensively in medical applications such as angioplasty, valvuloplasty, urological procedures and tracheal or gastric intubation.

For example, non-compliance and high tensile strength are less crucial in the case of the present invention's annular enclosing layer 12 of nuclear prosthesis 10. Annular enclosing layer 12 is not expected to be subjected to high bursting pressures because annular enclosing layer 12 is filled with curable in-situ rubber that is deformable, and because nuclear prosthesis 10 is contained within the confines of a closed space bordered by the native vertebral end-plates of the patient. Furthermore, annular enclosing layer 12 is disposed between annular reinforcement band 20 and nuclear enclosing layer 22, which restrain over-inflation of annular enclosing layer 12, thus further making non-compliance and high tensile strength less crucial. The thickness of the membrane (not shown) of which annular enclosing layer 12 is made need only be thick enough to provide a fluid-tight barrier to leakage of in-situ cured rubber. Accordingly, a thin membrane of 20 to 60 microns may be used to construct annular enclosing layer 12.

On the other hand, long-term structural integrity, moisture resistance (to avoid degeneration and to provide some protection to the rubber within annular enclosure 14) is of paramount importance to ensure durability. Other desirable attributes include kink resistance, low wall thickness, low tendency for pinholing, and ease of bonding and coating to other compounds.

Referring to FIGS. 4 through 9, 11A and 11B, sealing valve core 28 of the present invention is adapted to be disposed within annular enclosure 14 and is bondable to annular enclosing layer 12 by heat fusion, ultrasonic welding, hot mold bonding, crimping, or other similar bonding methods known in the art. Adhesive layers (not shown) may be used advantageously in combination to bond sealing valve core 28 of sealing valve assembly 26 to annular enclosing layer 12, although when the polymer material (not shown) of which sealing valve core 28 of sealing valve assembly 26 and annular enclosing layer 12 are made are similar, adhesives may be unnecessary.

As annular enclosing layer 12 is made from semi-compliant material (not shown), inflating annular enclosure 14 tends to exert a peel-away force on the bond between annular enclosing layer 12 and sealing valve core 28 of sealing valve assembly 26. To avoid this potential problem, nuclear slot 28a and annular slot 28b are formed along the surface of sealing valve core 28 adjacent inner margin 16 of annular enclosing layer 12, and are adapted to receive a portion of inner margin 16 of annular enclosing layer 12 and a portion of inner layer 30a of retaining ring 30. Annular slot 28b extends the radial circumference of sealing valve core 28. On the surface of sealing valve core 28 adjacent outer margin 18 of annular enclosing layer 12, annular slot 28 b receives a portion of outer margin 18 and a portion of outer layer 30b of retaining ring 30. In a preferred embodiment, the method of securing sealing valve core 28 of sealing valve assembly 26 to annular enclosing layer 12 includes the use of retaining ring 30 positioned over and crimped tightly around annular enclosing layer 12 such that inner layer 30a of retaining ring 30 is adjacent nuclear slot 28a, and outer layer 30b of retaining ring 30 is adjacent annular slot 28b. The entire connection of sealing valve core 28, annular enclosing layer 12 and retaining ring 30 is then thermally pressed to form a sealably bonded sealing valve core 28 within annular enclosure 14 resistant to separation from annular enclosing layer 12 during inflation.

Preferably, both sealing valve core 28 and the in-situ curable rubber injected into annular enclosure 14 are comprised of the same rubber material. When the in-situ curable rubber injected in annular enclosure 14 during inflation of nuclear prosthesis 10 solidifies, it bonds to sealing valve core 28. The result is that the distinction between sealing valve core 28 and the curable rubber disappears, and an integral annular enclosure 14 of unitary construction is created.

Referring to FIGS. 4, 9, 10 and 17 through 19, annular reinforcement band 20 is disclosed. Annular reinforcement band 20 of the present invention is preferably a semi-compliant multi-layered bio-compatible textile structure that provides a detent to maximal stretching of the circumference of nuclear prosthesis 10. Various parameters and properties of annular reinforcement band 20 may be adjusted to provide longitudinal flexibility and stretch, radial compliance, and kink resistance of annular reinforcement band 20. Such variations include varying the materials from which the fibers making up the layers 20a, 20b and 20c of annular reinforcement band 20 are formed, varying fiber density, varying fiber denier, varying braiding angles, varying the number of strands per filament, and varying heat-set conditions. These parameters are tailored to provide the desirable function required of a particular layer of annular reinforcement band 20, depending on the layer's position in annular reinforcement band 20. Generally, outer layers 20a should be substantially less compliant, and compliance the annular reinforcement band 20 should increase through intermediate layers 20b and inner layer 20c.

In a preferred embodiment, annular reinforcement band 20 is a three-dimensional structure that is formed by extending and interlocking at least one yarn of each layer of annular reinforcement band 20 with the adjacent layers. The multi-layered textile annular reinforcement band 20 shows a gradation of properties between its inner layers and outer layers. Referring to FIG. 9 and FIGS. 17 through 19, at least one, and preferably more than one outer layers 20a are preferably made of a warp knitted pattern of biocompatible fibers. This gives outer layers 20a of annular reinforcement band 20 the advantage of velour, high porosity surface, enhancing tissue in-growth, as well as resisting unraveling. The fibers of outer layers 20a may be of low denier and may be textured or non-textured.

At least one, and preferably more than one intermediate layers 20b may be formed from biocompatible fibers forming a plurality of loops which follow helical or spiral paths, which may also be wavy or serpentine, contributing to the compliance of annular reinforcement band 20. The fibers of intermediate layers 20b preferably include monofilaments of larger denier formed of durable material, such as polyethylene teraphthlate in braided or jersey patterns providing a load-bearing component, resistant to torsion and over-stretching. The fibers in intermediate layers 20b may be chosen to perform a gradation of properties between the mid or equatorial region of annular reinforcement band 20 towards the upper and lower axial margins thereof. In a preferred embodiment, the equatorial section of annular reinforcement band 20 is formed of monofilaments that are thicker, stronger and less compliant filaments, with tapering of these properties towards the upper and lower margins of annular reinforcement band 20. This renders annular reinforcement band 20 more resistant to kinking during stretching and radial compression of nuclear prosthesis 10 necessary to load nuclear prosthesis 10 within delivery apparatus 200.

Inner layer 20c of annular reinforcement band 20 is formed from more compliant and thinner biocompatible yarn. In one embodiment, inner layer 20c may include a fusible fiber (not shown) having a low melting temperature, heat-fusing annular reinforcement band 20 to an innermost layer of intermediate layers 20b and annular enclosing layer 12, enhancing ravel and fray resistance. In the preferred embodiment, annular reinforcement band 20 is not bonded to annular enclosing layer 12.

In the preferred embodiment of the present invention, synthetic yarns (not shown) which are not degraded by the body are used to form the textile annular reinforcement band 20. The yarns may be of the monofilament, multifilament or spun type, used in different combinations. Monofilaments are preferred in intermediate layers 20b, providing for a lower volume structure with comparable strength to the fiber bundles of the multifilament fibers. Multifilaments are preferred along inner layer 20c and outer layers 20a to increase flexibility. The yarns may be flat, textured, twisted, shrunk, or pre-shrunk. As discussed above, the yarn type and yarn denier for a particular layer of the textile annular reinforcement band 20 may be chosen to meet the design requirements of annular reinforcement band 20.

Figure 4:
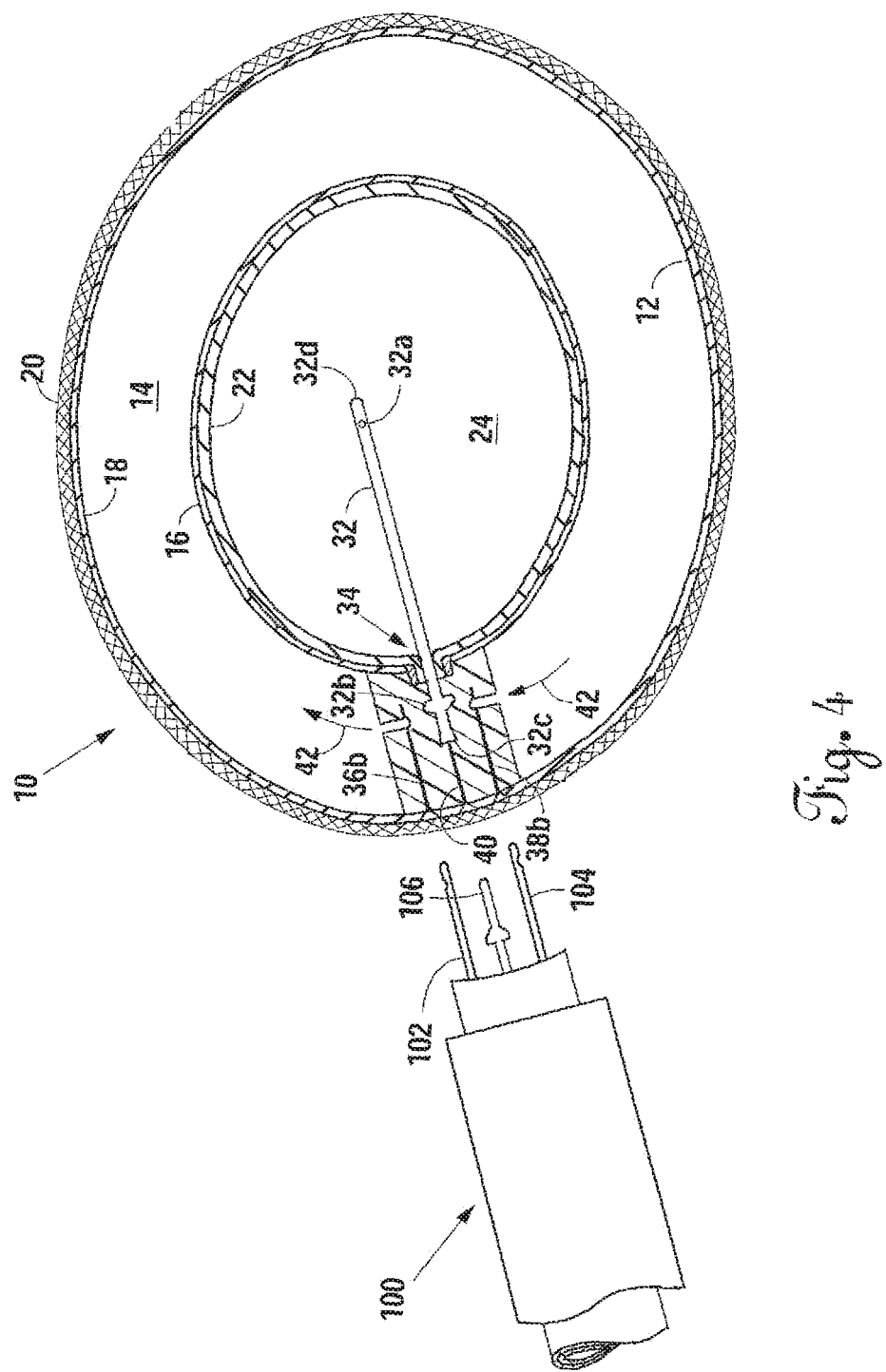
FIG. 4 is a sectional top view of the nuclear prosthesis and the inflation stylus of the present invention.
Figure 5:
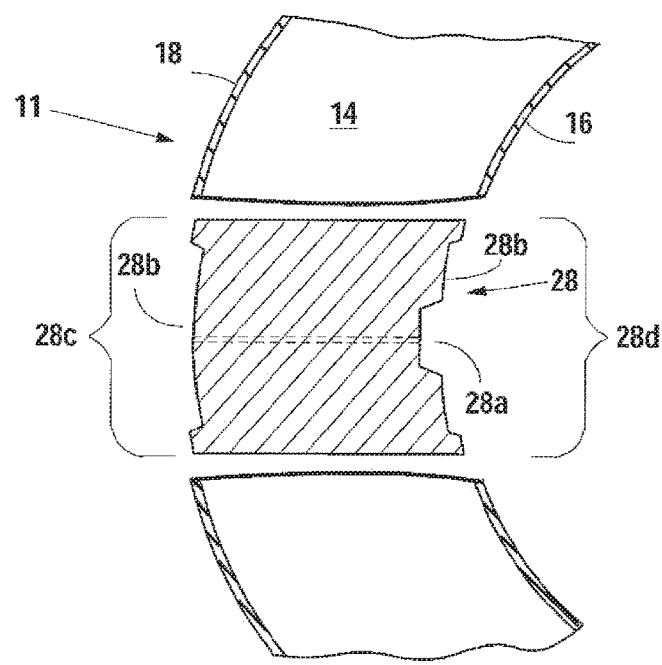
FIG. 5 is a sectional top partially exploded view of the sealing valve core of the sealing valve assembly of the nuclear prosthesis of the present invention.
Figure 6:
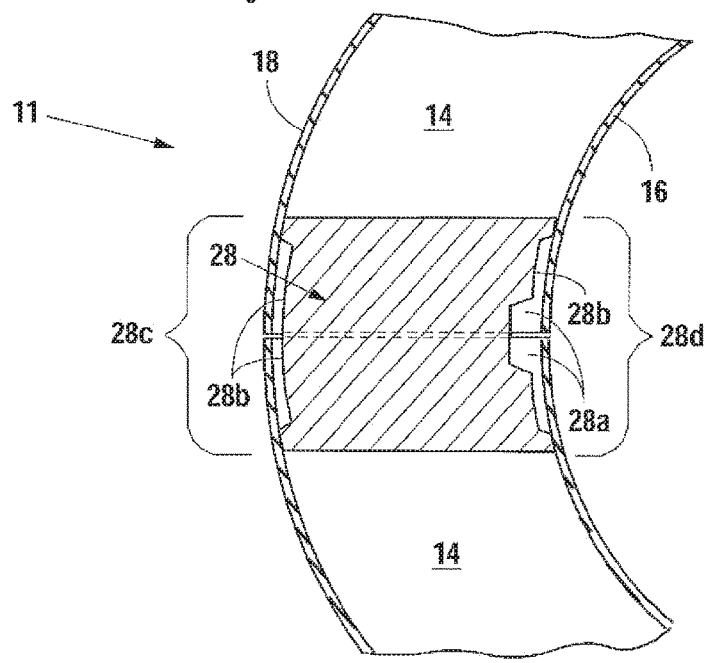
FIG. 6 is a sectional top view of the sealing valve core of the sealing valve assembly of the nuclear prosthesis of the present invention.
Figure 7:
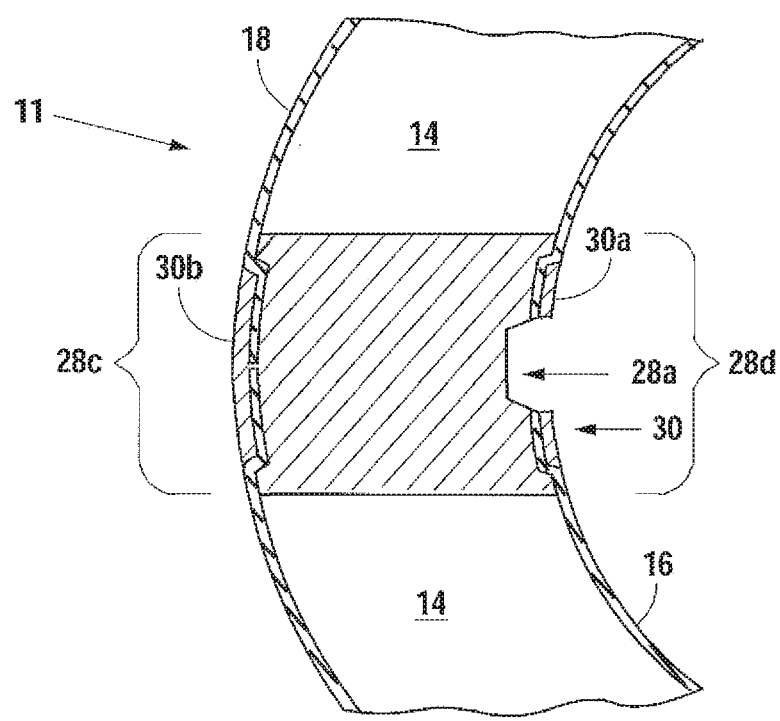
FIG. 7 is a sectional top view of the sealing valve core of the sealing valve assembly of the nuclear prosthesis of the present invention.

Referring to FIGS. 2, 3 and 4, nuclear enclosing layer 22 is essentially a discoid multilayered medical balloon which is fabricated by forming a plurality of polymeric layers (not shown) that converge on neck portion 22a of connector terminal 22b, adapted for fluid-tight bonding to indwelling catheter 32. Conventional balloon fabricating techniques are utilized to form a composite nuclear enclosing layer 22 of different polymeric materials (not shown) that are subjected to a stretch blow-molding operation in a heated mold (not shown). The resulting nuclear enclosing layer 22 of the present invention provides superior burst strength, superior abrasion resistance, and superior structural integrity, without significantly impairing the overall compressibility and gas-cushioning function of nuclear prosthesis 10.

Long-term maintenance of a gas cushion in an inflated state is perhaps the most demanding requirement of nuclear enclosure 24. Various approaches may be taken, including melt-blending the materials making up nuclear enclosing layer 22 and the use of multilayer fiber reinforced balloon structures (not shown) to make nuclear enclosing layer 22.

Referring to FIGS. 2, 3, 4 and 8, nuclear enclosing layer 22 has a neck portion 22a which is bonded to indwelling catheter 32, forming a secure connector terminal 22b. Indwelling catheter 32 has a proximal end 32c including bulbous portion 32b which is adapted to be coupled to nuclear access tube 106 inflation stylus 100, which is inserted through pathway 40 in sealing valve core 28 of sealing valve assembly 26. Bulbous portion 32b defines a bulbous portion that snaps into a corresponding bulbous region 32e in sealing valve core 28. Bulbous portion 32b is sealingly affixed to the corresponding bulbous portion 32e of sealing valve core 28, forming a fluid-tight bond with sealing valve core 28. Proximal end 32c of indwelling catheter 32 is in fluid communication with the distal end of nuclear access tube 106, within sealing valve core 28.

Nuclear enclosing layer 22 is sealingly mounted on the shaft of indwelling catheter 32. Preferably, neck portion 22a of nuclear enclosing layer 22 is thermally or meltably bonded to indwelling catheter 32. Connector terminal 22b and indwelling catheter 32 are all preferably made of melt compatible material. Connector terminal 22b may utilize a tie layer or "retaining collar" 22c formed of mutually bondable material that is slipped over neck portion 22a of nuclear enclosing layer 22. Retaining collar 22c is heated and crimped to simultaneously meltably join neck portion 22a of nuclear enclosing layer 22, retaining collar 22c, and indwelling catheter 32, making connector terminal 22b a permanent fluid-tight seal.

Indwelling catheter 32 defines a lumen with side pore 32a therein located proximal to closed tip 32d of indwelling catheter 32. After inflating nuclear prosthesis 10 within the nuclear space void of a patient, the lumen of indwelling catheter 32 can be permanently obstructed by a small sealing plug (not shown) introduced through proximal end 32c of indwelling catheter 32, and pushed into position with a guidewire (not shown) or other suitable positioning device. Pathway 40 of sealing valve core 28 collapses upon removal of inflation stylus 100, preventing back-up of the sealing plug within indwelling catheter 32.

Referring to FIGS. 1D, 2D and 3D, delivery apparatus 200 is disclosed. Prior to insertion of delivery apparatus 200 into the patient, a percutaneous access device (not shown) provides an access way or annular fenestration (not shown) into the inter-vertebral disc space of the patient, which is held open by an access cannula 202. Any percutaneous access device used for minimally invasive percutaneous procedures can be used to create the annular fenestration. Generally, such percutaneous access devices comprise a plurality of telescopically arranged cannulas (not shown). After creation of the annular fenestration, delivery apparatus 200 can be delivered within access cannula 202. Delivery apparatus 200 comprises a delivery cannula 204 with nuclear prosthesis 10 loaded therein, and a release cannula 206. Delivery apparatus 200, including nuclear prosthesis 10 and delivery cannula 204 which houses nuclear prosthesis 10 is provided, assembled and hermetically sealed so that loading or handling of nuclear prosthesis 10 is unnecessary during insertion and inflation thereof within the nuclear space void of the patient.

Still referring to FIGS. 1D, 2D, and 3D, delivery apparatus 200 of the present invention has oval inner and outer cross-section conforming to the cross sections of access cannula 202. Delivery apparatus 200 comprises a delivery cannula 204 having a wall of uniform thickness defining a cylindrical inner passage having a substantially oval cross section, and a substantially oval release cannula 206 located within the oval, cylindrical inner passage of delivery cannula 204. Inflation stylus 100 is slidably received within the oval release cannula 206.

Delivery apparatus 200 is slidably received internally of the access cannula 202, and is selectively extendible and retractable relative to access cannula 202 to facilitate proper placement of nuclear prosthesis 10 through the annular fenestration into the disc space void.

Figure 11B:
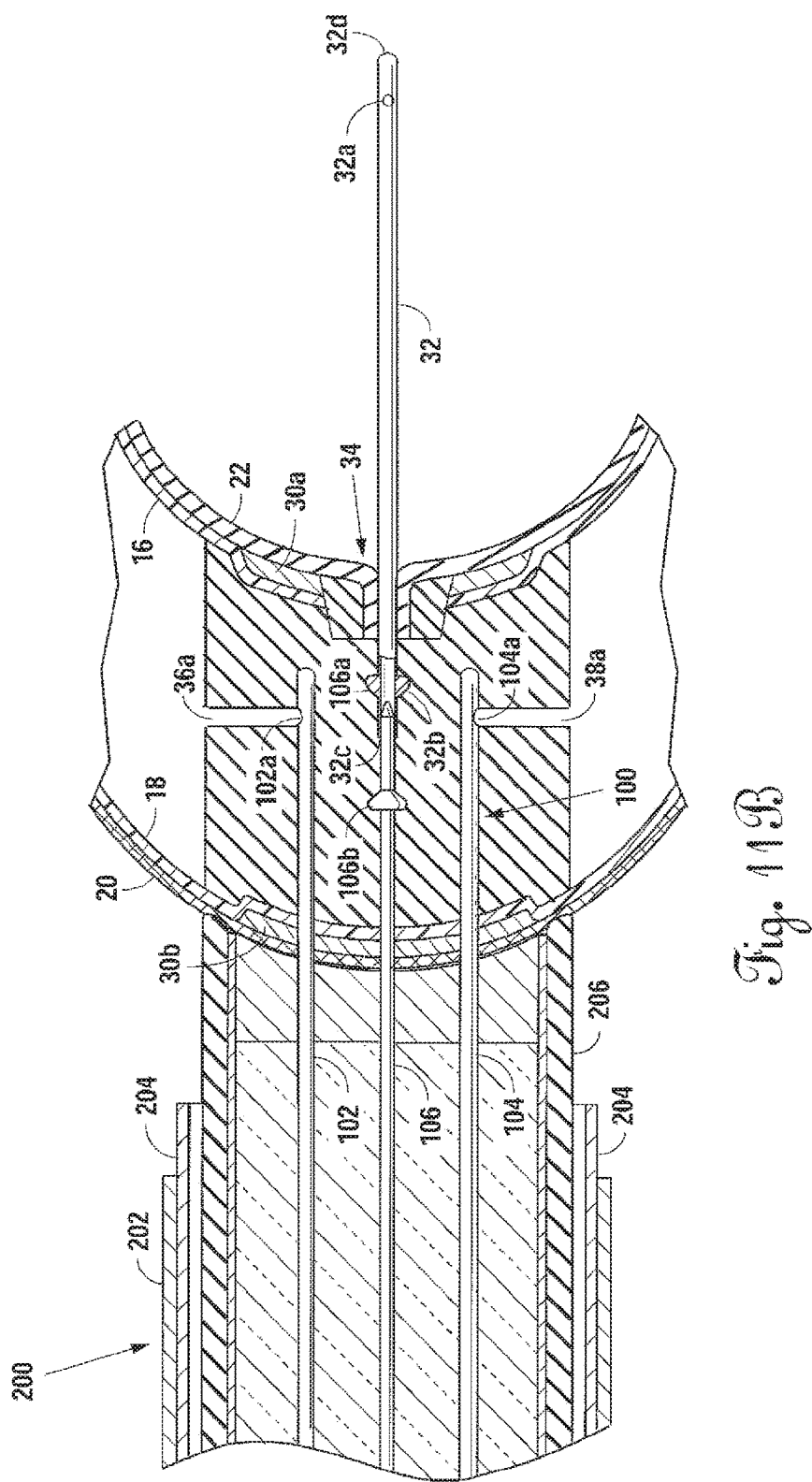

Referring to FIGS. 10 through 11B, delivery cannula 204 of delivery apparatus 200 encloses release cannula 206, which is telescopically slidable over inflation stylus 100. As previously discussed, inflation stylus 100 includes three inflation tubes 102, 104 and 106 extending from its tip. Inflation tubes 102, 104 and 106 are frictionally engaged to pathways 36b 38b and 40 (respectively) of sealing valve core 28. In a preferred embodiment, nuclear access tube 106 has a bulbous ridge 106b formed at its mid aspect that mates with a corresponding bulbous region 40b formed along passageway 40. The frictional engagement, as well as the engagement of bulbous ridge 106b with the bulbous region 40b provides a firm attachment of inflation stylus 100 to sealing valve core 28, while allowing inflation tubes 102, 104 and 106 to be withdrawn when sufficient force is applied to it.

The amount of force required to withdraw inflation stylus 100 from nuclear prosthesis 10 may be chosen by selecting the rigidity and modulus of elasticity forming sealing valve core 28 as well as selecting the size and geometry of the pathways 36b, 38b and 40 and bulbous ridge 106b. Generally, the amount of force required to release inflation stylus 100 from sealing valve core 28 must be more than the maximum inflation pressure experienced at the connection during inflation of nuclear prosthesis 10. It may be difficult to precisely control the force required to withdraw inflation stylus 100 from sealing valve core 28.

As may be appreciated, if this force is too great, sealing valve core 28 may be dislodged through the annulotomy, possibly causing tearing of the native annulus fibrosis. If the force required to withdraw inflation stylus 100 from sealing valve core 28 is too small, inflation stylus 100 may become prematurely detached from sealing valve core 28 during pressurizing and inflation of nuclear prosthesis 10.

Figure 12:
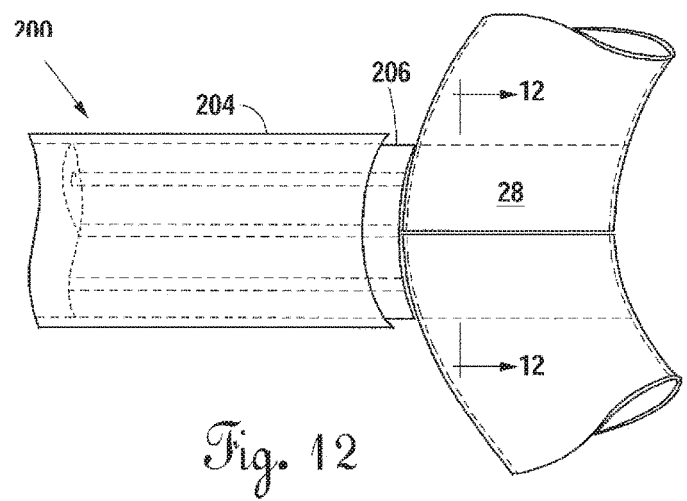
FIG. 12 is a side view of the release cannula of the delivery apparatus of the present invention interacting with the annular enclosing layer of the nuclear prosthesis of the present invention.

Referring to FIGS. 10 through 12, in a preferred embodiment, the release of inflation stylus 100 from sealing valve core 28 is obtained by utilizing release cannula 206 placed coaxially around inflation stylus 100. Release cannula 206 has a thick wall and a diameter smaller than the outer diameter of sealing valve core 28, such that its distal end engages sealing valve core 28 to, in effect, push sealing valve core 28 away from inflation stylus 100. A screw drive mechanism (not shown) is threadedly engaged with and coupled to the proximal end (not shown) of inflation stylus 100 and release cannula 206 to achieve smooth, efficient, and predictable disengagement of inflation stylus 100 from the sealing valve core 28.

The screw drive mechanism provides a mechanical advantage for withdrawing inflation stylus 100 from sealing valve core 28 at a controlled rate. A coupler (not shown) at the proximal end of inflation stylus 100 is adapted to engage the proximal end (not shown) of release cannula 206 to controllably extend and retract inflation stylus 100 and control its maximum travel. This can be done while the tip of release cannula 206 holds sealing valve core 28 stationary within annular enclosure 14. The extension and retraction capabilities of inflation stylus 100 (in unison or independent of release cannula 206) facilitate proper deployment and detachment of nuclear prosthesis 10 within the nuclear space void. Withdrawal of inflation stylus 100 may be achieved by merely turning a knob (not shown) on the screw drive mechanism, which causes inflation stylus 100 to retract axially with respect to release cannula 206, while sealing valve core 28 is held in place by the tip of release cannula 206, thereby selectively screw-engaging or disengaging release cannula 206.

The retracting motion continues until inflation tubes 102, 104 and 106 are completely disengaged from pathways 36*b*, 38*b* and 40, respectively, of sealing valve core 28. The screw drive mechanism may include a worm drive (not shown) that mates with teeth (not shown) formed on the exterior surface of inflation stylus 100 and release cannula 206. Clearly, a wide variety of mechanical linkages are available to extend and retract inflation stylus 100 and release cannula 206. It is particularly advantageous to provide a mechanism which allows independent, as well as linked and coordinated movements.

The knob may also be rotationally twisted in one direction during the loading of nuclear prosthesis 10 into delivery apparatus 200. In this case, release cannula 206 and inflation stylus 100 are retracted as one unit into delivery apparatus 200, pulling nuclear prosthesis 10 through a loading apparatus 300 and progressively radially compressing nuclear prosthesis 10 to a reduced-radius state until it is fully loaded within delivery cannula 204 of delivery apparatus 200. When the knob is rotationally twisted in the opposite direction, release cannula 206 and inflation stylus 100 extend as one unit extruding nuclear prosthesis 10 from the tip of delivery cannula 204 to achieve predictable and controlled incremental deployment within the nuclear space void.

Referring to FIGS. 1A, 2A and 3A, loading apparatus 300 has a first loading block 302 and a second loading block 304 traversed by mirror-image funnel-shaped passageways 306 and 308, respectively. The distal end of delivery apparatus 200 fits snugly but slidably within loading port 316 at a front end of first loading block 302. The apposing ends of first loading block 302 and second loading block 204 have the general size and configuration of an inflated nuclear prosthesis 10. Each funnel shaped passageway 306 and 308 of first loading block 302 and second loading block 304, respectively tapers down within each loading block 302 and 304 to a second, smaller configuration which has the general cross-sectional oblong configuration of delivery cannula 204 of delivery apparatus 200, and runs for a short distance in loading blocks 302 and 304, forming a smooth transition with the inner margin of delivery cannula 204 at the loading port 316 of first loading block 302.

Funnel passageways 306 and 308 of loading apparatus 300 define a tapered diamond-shaped space that geometrically and plastically deforms nuclear prosthesis 10 from a generally round, inflated configuration, as it is being deflated and pulled in opposing directions (as indicated by direction arrows 400 and 402) of the radial axis through the tapered funnel shaped passageways 306 and 308, and then loaded into delivery cannula 204 of delivery apparatus 200, which has been inserted into loading port 316 of first loading block 302.

Referring to FIGS. 1A through 3C, as nuclear prosthesis 10 is pulled and stretched in opposing directions 400 and 402 within the diamond-shaped passageway defined by funnel shaped passageways 306 and 308, nuclear prosthesis is progressively radially approximated to a reduced-radius state. Simultaneously, annular enclosure 14 is deflated, approximating inner margin 16 and outer margin 18 of annular enclosing layer 12 into the thin substantially "C" shaped configuration, which assumes a more acute curvature as nuclear prosthesis 10 is stretched.

Annular enclosing layer 12 is stretched in a radial direction diametrically opposite to loading port 316 and delivery apparatus 200 by a traction band 322 removably wrapped around annular enclosing layer 12 at a position diametrically opposite the position of loading port 316. In one embodiment, removable traction band 322 is a rubber band. However, any suitable band made of any suitable material can be used as traction band 322, so long as it allows for removable attachment to annular enclosing layer 12 and is capable of stretching nuclear prosthesis 10 in a direction diametrically opposite the direction delivery apparatus 200 stretches nuclear prosthesis 10. As nuclear prosthesis 10 reaches the small end of the diamond-shaped passageway defined by funnel shaped passageways 306 and 308, annular enclosing layer 12 is wrapped tightly and folded compactly around nuclear enclosing layer 22 and indwelling catheter 32, into the smallest possible cross-section, and is withdrawn into delivery cannula 204 of delivery apparatus 200. The folded nuclear prosthesis 10 fits loosely within delivery cannula 204, allowing achievement of unhindered deployment into the nuclear space void.

The inner surfaces of loading blocks 302 and 304 are preferably lined with a water-soluble lubricious hydrophilic coating (not shown) to lubricate the contact surfaces between loading blocks 302 and 304 and nuclear prosthesis 10 during loading thereof onto delivery apparatus 200.

During the loading process, nuclear prosthesis 10 is deflated, stretched and radially compressed so as to adopt a low-profile configuration within the delivery cannula. Referring to FIGS. 3A and 3D, folded nuclear prosthesis 10 is shown releasably attached to the distal end of inflation stylus 100, which is surrounded by release cannula 206 and housed within the delivery cannula 204. Delivery apparatus 200 passes through access cannula 202. As previously discussed, nuclear prosthesis 10 is secured to inflation stylus 100, by way of inflation tubes 102, 104 and 106 projecting from the distal tip of inflation stylus 100 and inserted into corresponding passageways 36b, 38b and 40, respectively, in sealing valve core 28 of nuclear prosthesis 10. When the inflation stylus 100—release cannula 206 assembly is retracted within delivery cannula 204, the loaded nuclear prosthesis 10 is pulled into the delivery cannula 204.

It should be appreciated by one skilled in the art that once the deflated nuclear prosthesis 10 is delivered into the nuclear space void, an inflation-assisting device (not shown) or fluid delivery apparatus (not shown) introduces the in-situ curable rubber into annular enclosure 14 and the liquid and/or gas into nuclear enclosure 24. It should be understood to one of ordinary skill in the art that any device, apparatus and/or system suitable for injecting fluid can be used to inflate nuclear prosthesis 10 could be used. Furthermore, fluid can be injected into nuclear prosthesis 10 manually using a syringe (not shown) connected to the tubes 102, 104 and 106 of inflation stylus 100.

Although the invention has been described with reference to specific embodiments, this description is not meant to be construed in a limited sense. Various modifications of the disclosed embodiments, as well as alternative embodiments of the invention will become apparent to persons skilled in the art upon the reference to the description of the invention. It is therefore contemplated that the appended claims will cover such modifications that fall within the scope of the invention.

We claim:

1. A method of implanting a nuclear prosthesis into a de-nucleated inter-vertebral disc space comprising:
   providing a nuclear prosthesis comprising:
      an annular tubular elastomeric enclosure forming a fluid-tight inflatable annular chamber, the annular enclosure having an inner region;
      an inflatable nuclear enclosure forming a gas-tight inflatable nuclear chamber, the nuclear enclosure being disposed within the inner region of the annular enclosure; and
      a resilient core secured to the annular enclosure, the resilient core having at least a first channel for providing closable access to the annular chamber and a second channel for providing access to the nuclear chamber;
   inserting the nuclear prosthesis into a de-nucleated inter-vertebral disc space;
   inflating the nuclear enclosure with a pressurized fluid comprising saline;
   inflating the annular enclosure with a pressurized fluid comprising a curable elastomeric material; and
   allowing the curable elastomeric material to cure.

2. The method of claim 1, further comprising replacing the saline in the nuclear enclosure with gas.

3. The method of claim 2, further comprising sealing the second channel to seal the gas in the nuclear enclosure.

4. The method of claim 1, further comprising providing an annular reinforcement band around the annular enclosure.

5. The method of claim 1, further comprising loading said nuclear prosthesis into a delivery apparatus.

6. The method of claim 5, wherein said delivery apparatus comprises a delivery cannula and a release cannula.

7. The method of claim 6, further comprising manipulating the release cannula to release the nuclear prosthesis from the delivery apparatus.

8. A method of implanting a nuclear prosthesis comprising:
   creating a de-nucleated inter-vertebral disc space by performing a percutaneous nuclectomy through a percutaneous access device;
   inserting a delivery apparatus carrying a nuclear prosthesis into the de-nucleated inter-vertebral disc space, said nuclear prosthesis comprising:
      an annular tubular elastomeric enclosure forming a fluid-tight inflatable annular chamber, the annular enclosure having an outer perimeter and an inner region;
      an inflatable nuclear enclosure forming a gas-tight inflatable nuclear chamber, the nuclear enclosure being disposed at least partially within the inner region of the annular enclosure; and
      a resilient core secured to the annular enclosure, the resilient core having at least a first channel for providing closable access to the annular chamber and a second channel for providing access to the nuclear chamber;
   deploying the nuclear prosthesis into the de-nucleated inter-vertebral disc space;
   inflating the nuclear enclosure with a pressurized fluid comprising saline;
   inflating the annular tubular enclosure with a pressurized fluid comprising a curable elastomeric material; and
   allowing the curable elastomeric material to cure.

9. The method of claim 8, further comprising replacing the saline in the nuclear enclosure with gas.

10. The method of claim 9, further comprising sealing the second channel to seal the gas in the nuclear enclosure.

11. The method of claim 8, wherein said delivery apparatus comprises a delivery cannula and a release cannula.

12. The method of claim 11, further comprising manipulating the release cannula to release the nuclear prosthesis from the delivery apparatus.

13. The method of claim 12, further comprising removing the delivery cannula.

14. A method of implanting a nuclear prosthesis into a de-nucleated inter-vertebral disc space comprising:
   creating a de-nucleated inter-vertebral disc space by performing a percutaneous nuclectomy through a percutaneous access device;
   providing a system for inserting a nuclear prosthesis into the de-nucleated inter-vertebral disc space, said system comprising:
      a nuclear prosthesis comprising an annular tubular elastomeric enclosure forming a fluid-tight inflatable annular chamber, the annular enclosure having an outer perimeter and an inner region; an inflatable nuclear enclosure forming a gas-tight inflatable nuclear chamber, the nuclear enclosure being disposed at least partially within the inner region of the annular enclosure; and a resilient core secured to the annular enclosure, the resilient core having at least a first channel for providing closable access to the annular chamber and a second channel for providing access to the nuclear chamber;
      a delivery apparatus for percutaneously delivering the nuclear prosthesis, comprising a delivery cannula and a release cannula; and an inflation stylus for inflating a the nuclear prosthesis, the inflation stylus at least partially within the delivery cannula and detachably connected to the nuclear prosthesis;

deploying the nuclear prosthesis into the de-nucleated inter-vertebral disc space using the delivery apparatus;

inflating the nuclear enclosure with a pressurized fluid comprising saline using the inflation stylus;

inflating the annular tubular enclosure with a pressurized fluid comprising a curable elastomeric material using the inflation stylus; and allowing the curable elastomeric material to cure.

15. The method of claim 14, further comprising replacing the saline in the nuclear enclosure with gas using the inflation stylus.

16. The method of claim 15, further comprising sealing the second channel to seal the gas in the nuclear enclosure.

17. The method of claim 14, further comprising manipulating the release cannula to release the nuclear prosthesis from the delivery apparatus.

18. The method of claim 17, further comprising removing the delivery cannula.

* * * * *